United States Patent
Abken et al.

(10) Patent No.: US 11,512,139 B2
(45) Date of Patent: Nov. 29, 2022

(54) CHIMERIC ANTIGEN RECEPTOR WITH CYTOKINE RECEPTOR ACTIVATING OR BLOCKING DOMAIN

(71) Applicant: Miltenyi Biotec GmbH, Bergisch Gladbach (DE)

(72) Inventors: Hinrich Abken, Meudt (DE); Andreas Hombach, Bruhl (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 0 days.

(21) Appl. No.: 16/065,282

(22) PCT Filed: Dec. 20, 2016

(86) PCT No.: PCT/EP2016/081944
§ 371 (c)(1),
(2) Date: Jun. 22, 2018

(87) PCT Pub. No.: WO2017/108805
PCT Pub. Date: Jun. 29, 2017

(65) Prior Publication Data
US 2021/0040226 A1    Feb. 11, 2021

(30) Foreign Application Priority Data
Dec. 23, 2015 (EP) ..................... 15202625

(51) Int. Cl.
| C07K 16/30 | (2006.01) |
| A61K 39/00 | (2006.01) |
| C07K 14/54 | (2006.01) |
| C07K 14/725 | (2006.01) |
| C07K 14/705 | (2006.01) |

(52) U.S. Cl.
CPC .... *C07K 16/3007* (2013.01); *A61K 39/00117* (2018.08); *C07K 14/5434* (2013.01); *C07K 14/7051* (2013.01); *C07K 14/70521* (2013.01); *A61K 2039/505* (2013.01); *C07K 2317/622* (2013.01); *C07K 2317/64* (2013.01)

(58) Field of Classification Search
CPC ............ C07K 16/3007; C07K 14/5434; C07K 14/7051; C07K 14/70521; A61K 39/00117
See application file for complete search history.

(56) References Cited

U.S. PATENT DOCUMENTS

| 7,514,537 B2 | 4/2009 | Jensen |
| 10,273,295 B2 | 4/2019 | Bosio et al. |
| 10,767,184 B2 * | 9/2020 | Kochenderfer .... C07K 14/7051 |
| 2014/0134142 A1 * | 5/2014 | Smith ................. A61P 43/00 424/93.21 |
| 2014/0255363 A1 | 9/2014 | Metelitsa et al. |
| 2015/0017121 A1 | 1/2015 | Becher et al. |
| 2020/0061113 A1 * | 2/2020 | Kassim ............ G01N 33/5005 |

FOREIGN PATENT DOCUMENTS

| CN | 102119175 A | 7/2011 |
| CN | 102399292 A | 4/2012 |
| CN | 102712933 A | 10/2012 |
| CN | 103289955 A | 9/2013 |
| EP | 2711418 | 3/2014 |
| WO | WO 0124832 A2 | 4/2001 |
| WO | WO 2009/072003 | 6/2009 |
| WO | WO 2013/040557 | 3/2013 |
| WO | WO 2014/127261 | 8/2014 |
| WO | WO 2015/017214 | 2/2015 |
| WO | WO 2015028444 A1 | 3/2015 |
| WO | WO 2015/090229 | 6/2015 |
| WO | WO 2015/142661 | 9/2015 |
| WO | WO 2015132604 A1 | 9/2015 |
| WO | WO 2015/150771 | 10/2015 |
| WO | WO 2016201394 | 12/2016 |
| WO | WO 2017062820 | 4/2017 |
| WO | WO 2018045325 | 3/2018 |
| WO | WO 2018175988 | 9/2018 |

OTHER PUBLICATIONS

The Merck Manuals Online Medical Library, [online]. Merck Research Laboratories, 2006-2007. [retrieved on Oct. 19, 2020]. Retrieved from the Internet: < URL: https://www.merckmanuals.com/professional/hematology-and-oncology/overview-of-cancer/cellular-and-molecular-basis-of-cancer >. (Year: 2020).*
Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression", Cancer Res. Sep. 1, 2011;71(17):5697-706. (Year: 2011).*
Maher et al. "CAR Mechanics: Driving T Cells into the MUC of Cancer", (Cancer Res. Jun. 1, 2009;69(11):4559-62). (Year: 2009).*
Jiang et al. "Coadministration of Interleukin 12 Expression Vector with Antigen 2 cDNA Enhances Induction of Protective Immunity against Coccidioides immitis", (Infect. Immun. 67 (11), 5848-5853 (1999)). (Year: 1999).*
Duffy et al. "Clinical utility of biochemical markers in colorectal cancer: European Group on Tumour Markers (EGTM) guidelines", Eur J Cancer. Apr. 2003;39(6):718-27 (Year: 2003).*
Grada et al. "TanCAR: A Novel Bispecific Chimeric Antigen Receptor for Cancer Immunotherapy", Mol Ther Nucleic Acids. Jul. 9, 2013;2(7):e105 (Year: 2013).*
Fidler. "Biological heterogeneity of cancer", Human Vaccines & Immunotherapeutics 8:8, 1141-1142 (Year: 2012).*

(Continued)

*Primary Examiner* — Amy E Juedes
*Assistant Examiner* — Peter Johansen
(74) *Attorney, Agent, or Firm* — Fish & Richardson P.C.

(57) ABSTRACT

The present invention provides a chimeric antigen receptor (CAR), comprising an extracellular part, at least one intracellular signaling domain, and at least one transmembrane domain, wherein the extracellular part of said CAR comprises a) at least one antigen binding domain, and b) at least one cytokine receptor activating or blocking domain. The invention also provides isolated nucleic acid molecule(s) encoding for the said CAR, a cell comprising said nucleic acid molecule(s), a cell expressing said CAR and therapeutic uses of said CAR.

11 Claims, 15 Drawing Sheets

Specification includes a Sequence Listing.

(56) References Cited

OTHER PUBLICATIONS

International Search Report and Written Opinion issued in PCT/EP2016/081944, dated Mar. 16, 2017 (5 pages).

Chmielewski et al., "IL-12 Release by Engineered T Cells Expressing Chimeric Antigen Receptors Can Effectively Muster an Antigen-Independent Macrophage Response on Tumor Cells that Have Shut Down Tumor Antigen Epression", Cancer Research, vol. 71, No. 17, pp. 5697-5706 (2011).

Chmielewski et al., "Trucks: the fourth generation of CARs", Expert Opinion on Biological Therapy, vol. 15, No. 8, pp. 1145-1154 (2015).

Sadelain et al., "The promise and potential pitfalls of chimeric antigen receptors", Current Opinion in Immunology, vol. 21, No. 2, pp. 215-223 (2009).

Chmielewski et al, "Of CARs and TRUCKs: chimeric antigen receptor (CAR) T cells engineered with an inducible cytokine to modulate the tumor stroma", Immunological Reviews, vol. 257, No. 1, pp. 83-90 (2014).

Blat et al., Suppression of murine colitis and its associated cancer by carcinoembryonic antigen-specific regulatory T cells., Molecular Therapy: The Journal of the American Society of Gene Therapy, vol. 22, No. 5, pp. 1018-1028 (2014).

Burga et al., "Liver myeloid-derived suppressor cells expand in response to liver metastases in mice and inhibit the anti-tumor efficacy of anti-CEA CAR-T.", Cancer Immunology, Immunotherapy, pp. 817-829 (2015).

Figueroa et al., "A Chimeric Antigen Receptor Engineering: A Right Step in the Evolution of Adoptive Cellular Immunotherapy", International Reviews of Immunology, Hardwood Academic Publishers, vol. 34, pp. 154-187 (2015).

Holzinger et al., "The growing world of CAR T cell trials: a svstematic review," Cancer Immunol. Immunother., Sep. 2016, 65(12): 1433-1450.

Wu et al., "Remote control of therapeutic T cells through a small molecule-gated chimeric receptor," Science, Oct. 16, 2015, 350(6258): 293-303.

Krenciute et al., "Characterization and functional analysis of scFv-based chimeric antigen receptors to redirect T cells to IL13Rα2-positive glioma," Molecular Therapy, Feb. 1, 2016, 24(2):354-63.

Labanieh et al., "Programming CAR-T cells to kill cancer," Nature Biomedical Engineering, Jun. 2018, 2(6):377-91.

Lerner, "Combinatorial antibody libraries: new advances, new immunological insights," Nature Reviews Immunology, Aug. 2016, 16(8):498-508.

Di Stasi et al., "T lymphocytes coexpressing CCR4 and a chimeric antigen receptor targeting CD30 have improved homing and anti-tumor activity in a Hodgkin tumor model," Blood, The Journal of the American Society of Hematology, Jun. 18, 2009, 113(25):6392-402.

Haso et al., "Anti-CD22-chimeric antigen receptors targeting B-cell precursor acute lymphoblastic leukemia," Blood, The Journal of the American Society of Hematology, Feb. 14, 2013, 121(7):1165-74.

Jensen et al., "Anti-transgene rejection responses contribute to attenuated persistence of adoptively transferred CD20/CD19-specific chimeric antigen receptor redirected T cells in humans," Biology of Blood and Marrow Transplantation, Sep. 1, 2010, 16(9):1245-56.

Kochenderfer et al., "Construction and pre-clinical evaluation of an anti-CD19 chimeric antigen receptor," Journal of Immunotherapy, Sep. 2009, 32(7):689, 26 pages.

Lamers et al., "Treatment of metastatic renal cell carcinoma with CAIX CAR-engineered T cells: clinical evaluation and management of on-target toxicity," Molecular Therapy, Apr. 1, 2013, 21(4):904-12.

Lanitis et al., "Redirected antitumor activity of primary human lymphocytes transduced with a fully human anti-mesothelin chimeric receptor," Molecular Therapy, Mar. 2012, 20(3):633-43.

Tettamanti et al., "Targeting of acute myeloid leukaemia by cytokine-induced killer cells redirected with a novel CD 123-specific chimeric antigen receptor," British Journal of Haematology, May 2013, 161(3):389-401.

Wang et al., "Specificity redirection by CAR with human VEGFR-1 affinity endows T lymphocytes with tumor-killing ability and anti-angiogenic potency," Gene Therapy, May 2013, 20(10):970-8.

Zhao et al., "A herceptin-based chimeric antigen receptor with modified signaling domains leads to enhanced survival of transduced T lymphocytes and antitumor activity," The Journal of Immunology, Nov. 1, 2009, 183(9):5563-74.

GenBank Accession No. AF411293.1, "Synthetic construct bioactive single-chain murine interleukin 12 mRNA, complete CDS," Sep. 10, 2001, 2 pages.

GenBank Accession No. EU645745.1, "Synthetic construct anti-MUC1 T cell chimeric receptor gene, complete CDS," Apr. 29, 2008, 2 pages.

Katz et al., "Phase I Hepatic Immunotherapy for Metastases Study of Intra-Arterial Chimeric Antigen Receptor—Modified T-cell Therapy for CEA+ Liver Metastases Hepatic Artery CAR-T Infusions," Clinical Cancer Research, Jul. 15, 2015, 21(14):3149, 36 pages.

Ma et al., "Specific cytotoxicity of MUC1 chimeric antigen receptor-engineered Jurkat T cells against hepatocellular carcinoma," Journal of the Second Military Medical Academy, 2014, 5:1177, 2 pages (abstract only).

\* cited by examiner

A: anti-CEA-CAR (BW431/26scFv-Fc-CD28dzeta)

B: anti-CEA-IL12-CAR (BW431/26scFv-IL12-Fc-CD28dzeta)

A: anti-Muc1-CAR (BW431/26scFv-Fc-CD28dzeta)

B: anti-Muc1-IL12-CAR (BW431/26scFv-IL12-Fc-CD28dzeta)

IL-7-anti-CEA-CAR (IL7-BW431/26scFv-Fc-CD28d-CD3zeta)

CHIMERIC ANTIGEN RECEPTOR WITH CYTOKINE RECEPTOR ACTIVATING OR BLOCKING DOMAIN

CROSS-REFERENCE TO RELATED APPLICATIONS

This application is a 371 U.S. National Stage Application of PCT Application No. PCT/EP2016/081944, filed on Dec. 20, 2016, which claims the benefit of priority under 35 U.S.C. § 119(b) to European Application No. EP15202625.8, filed on Dec. 23, 2015, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created on Jun. 20, 2018, is named 42449-0006US1_SL.txt and is 52 kilobytes in size.

FIELD OF THE INVENTION

The present invention relates to the field of chimeric antigen receptors, in particular to chimeric antigen receptors comprising at least one antigen binding domain, at least one cytokine receptor activating or blocking domain, a facultative extracellular spacer domain linked to a transmembrane and an intracellular signaling domain, to cells expressing the same, and to therapeutic uses thereof.

BACKGROUND OF THE INVENTION

The treatment of malignant diseases by adoptive cell therapy is gaining major interest, based on the general assumption that the immune system can control cancer in the long-term. Tumor-infiltrating lymphocytes (TILs) isolated from tumor lesions, expanded ex vivo, and re-infused to the patient have produced encouraging results in the therapy of metastatic melanoma. As the specificity of those T cells is frequently not known and TILs can often not be isolated to sufficient numbers from other tumor entities, strategies were elaborated to engraft patients' T cells ex vivo with pre-defined specificity for cancer cells, by engineering with a T cell receptor (TCR) or a recombinant chimeric antigen receptor (CAR) ('T-body'). In contrast to the TCR, the CAR is composed of one polypeptide chain with an extracellular antigen-binding domain derived from an antibody, mostly a single-chain fragment of variable region (scFv) antibody, and an intracellular signaling chain, frequently the TCR-derived CD3zeta chain. The antibody domain mediates target recognition independently of major histocompatibility complex (MHC) and enables the targeting of a plethora of antigens, including proteins, carbohydrates and gangliosides, as long as the antigen is present on the surface of the target cell. Antigen engagement by the CAR induces synapse formation and downstream signaling through the cascade of TCR-associated kinases, finally producing increased cytokine secretion, T cell amplification, and cytotoxicity. Modification of the CAR structure and in particular of the individual CAR domains to optimize redirected T cell function has long been an aspect of preclinical research. Second-generation CARs were engineered by adding a co-stimulatory domain to the basic CD3zeta signaling chain to boost the response and to prolong T cell persistence; third generation CARs harbor two co-stimulatory domains to fine-tune the redirected T cell response.

In U.S. Pat. No. 7,514,537B2 chimeric transmembrane immunoreceptors, named "zetakines" are disclosed. They are comprised of an extracellular domain comprising a soluble receptor ligand, e.g. a cytokine, linked to a support region capable of tethering the extracellular domain to a cell surface, a transmembrane region and an intracellular signaling domain. Zetakines, when expressed on the surface of T lymphocytes, direct T cell activity to those specific cells expressing a receptor for which the soluble receptor ligand is specific as the soluble receptor ligand is identical with the antigen binding domain of the chimeric transmembrane immunoreceptor. A zetakine does not affect the homeostatic milieu of cytokines in a patient to which it might be applied.

Despite remarkable success in the treatment of hematologic malignancies, the T-body strategy is facing a number of limitations when targeting solid tumor lesions; some of them represent a more general limitation of antigen-redirected strategies. As the disease progresses, cancer cells gain considerable variability in phenotype and function, resulting in antigen-loss tumor cell variants that are invisible to CAR or TCR modified T-cells. In addition, several other mechanisms add to the reduction in the anti-tumor efficacy of specific T-cells, for instance, increasing resistance to a cytolytic T cell attack due to defects in the apoptosis pathway, a stroma, which is less penetrable to T cells and a milieu, which actively represses immune cell activation by various means, including regulatory T (Treg) cells, myeloid-derived suppressor cells (MDSCs), and macrophages. These and other factors facilitate tumor relapse, despite high numbers of circulating tumor-specific T cells. A number of efforts are currently being made to overcome these limitations, for instance, by the optimization of target binding, improving T cell survival, and providing a favorable homeostatic milieu. A recently described strategy addresses the elimination of antigen-loss cancer cell variants in addition to the mentioned drawbacks by using CAR-engineered T cells as production facilities, which release a transgenic cytokine into the targeted tumor tissue to recruit additional immune cells for the fight against those cancer cells that are invisible to CAR T cells (Chmielewski et al, Immunological Reviews 2014, Vol. 257: 83-90).

TRUCKs (T cells redirected for universal cytokine killing) are CAR-redirected T cells used as vehicles to produce and release a transgenic product that accumulates in the targeted tissue. The product, mostly a pro-inflammatory cytokine, may be constitutively produced or induced once the T cell is activated by the CAR in the targeted tissue. The accumulation of a transgenic pro-inflammatory cytokine is aimed at recruiting a second wave of immune cells in a local restricted fashion to initiate an attack toward those cancer cells which are invisible to CAR T cells. Other producer cells than T cells, like NK cells, may also be used as CAR-redirected vehicles producing a payload upon CAR activation in the targeted tissue. The feasibility of the TRUCK strategy was recently demonstrated by the local accumulation of IL-12, which cannot be systemically given in therapeutic doses due to the extraordinary IL-12 toxicity. T cells redirected by a tumor-targeting CAR and additionally engineered with a CAR-inducible IL-12 (iIL-12) cassette secrete IL-12 upon CAR engagement of cognate antigen (Chmielewski Cancer Res 2011; 71:5697-5706); without CAR signaling, no IL-12 release occurred.

TRUCK mediated release of IL-12 is locally restricted, however, at risk of accumulating IL-12 in an "off-tumor" environment.

Interleukin 12 (IL-12) is an interleukin that is naturally produced by dendritic cells, macrophages, neutrophils, and human B-lymphoblastoid cells (NC-37) in response to antigenic stimulation.

It is a heterodimeric cytokine encoded by two separate genes, IL-12A (p35) and IL-12B (p40). The active heterodimer (referred to as 'p70'), and a homodimer of p40 are formed following protein synthesis. IL-12 is involved in the differentiation of naive T cells into Th1 cells. It is known as a T cell-stimulating factor, which can stimulate the growth and function of T cells. It stimulates the production of interferon-gamma (IFN-γ) and tumor necrosis factor-alpha (TNF-α) from T cells and natural killer (NK) cells, and reduces IL-4 mediated suppression of IFN-γ. IL-12 plays an important role in the activities of natural killer cells and T lymphocytes. IL-12 mediates enhancement of the cytotoxic activity of NK cells and CD8+ cytotoxic T lymphocytes.

IL-12 binds to the IL-12 receptor, which is a heterodimeric receptor formed by IL-12R-β1 and IL-12R-β2. IL-12R-β2 is considered to play a key role in IL-12 function, since it is found on activated T cells.

There is a need in the art for an improved CAR, especially for a CAR which can interact controllably with the cytokine receptor—cytokine system in a subject, when the CAR is expressed on immune cells.

SUMMARY OF THE INVENTION

The present invention provides a CAR which harbors at least one cytokine receptor activating or blocking domain, e.g. at least one cytokine of interest, as an additional module in the extracellular part of the CAR. The CAR as disclosed herein is a trans-activating CAR. The trans-activating CAR, when expressed on the surface of white blood cells (immune cells) direct trans-activity of those cells against target cells expressing the antigen which is recognized by said at least one antigen binding domain of the trans-activating CAR.

Trans-activity means the characteristics of the CAR of the invention, that the CAR of the invention comprises at least one domain, i.e. the cytokine receptor activating or blocking domain, that, when expressed on the surface of white blood cells, triggers an activity on the target cell, on the white blood cell expressing said CAR or on another cell, wherein said triggered activity is independent from the binding of the antigen of the target cell by the antigen binding domain of said CAR. Said triggered activity may be the activation of a cytokine receptor resulting for example in a release of the given cytokine (when said domain is a cytokine receptor activating domain) or may be the blocking of a cytokine receptor resulting for example in a decrease or inhibition of the release of a given cytokine (when said domain is a cytokine receptor blocking domain).

Surprisingly it was found that a cytokine receptor activating domain such as the single chain p40-p35 IL-12 (a recombinant variant of the IL-12) which is integrated into the extracellular part of a CAR can interact and activate the matching cytokine receptor. For example, IL-12 or a functional fragment thereof integrated into the extracellular part of a CAR activates the IL-12 receptor of the immune effector cell, e.g. T cells expressing said CAR, resulting in a synergistic T cell activation upon CAR engagement of target, e.g., indicated by the increase in the IFN-γ release. The CAR containing cell (hereafter "CAR-cell") attack benefits from the cytokine mediated signaling with respect to a prolonged and improved immune response and persistence in the targeted tumor tissue. IL-12 initiates and promotes a number of functions including the activation of T cells, NK cells, myeloid derived cells, promotion of T helper-1 polarization and reversion of T helper-2 polarization, improvement of MHC class I presentation, increase in chemokine secretion like IP-10 and MIG, altering the extracellular matrix and decrease in angiogenesis.

The IL-12 p40 homodimer is an example for a cytokine receptor blocking domain of the CAR as disclosed herein.

The invention also provides isolated nucleic acid molecule(s) encoding for the said CAR, a cell comprising said nucleic acid molecule(s), a cell expressing said CAR and therapeutic uses of said CAR.

Conditioned and non-conditioned CAR T cells (2.5×10(4)/well) and anti-CEA-IL12-CAR T cells were co-cultivated for 48 h with CEA+ LS174T or Skov3 tumor cells and for control with CEA− Colo320 tumor cells (each 2.5×10(4)/well), respectively. After 48 h target cell viability was determined by a colorimetric tetrazolium-salt based XTT assay. Cytotoxicity was calculated by 100−viability [%]. Data represent mean of triplicates+−standard deviation (SD).

Figure 8:
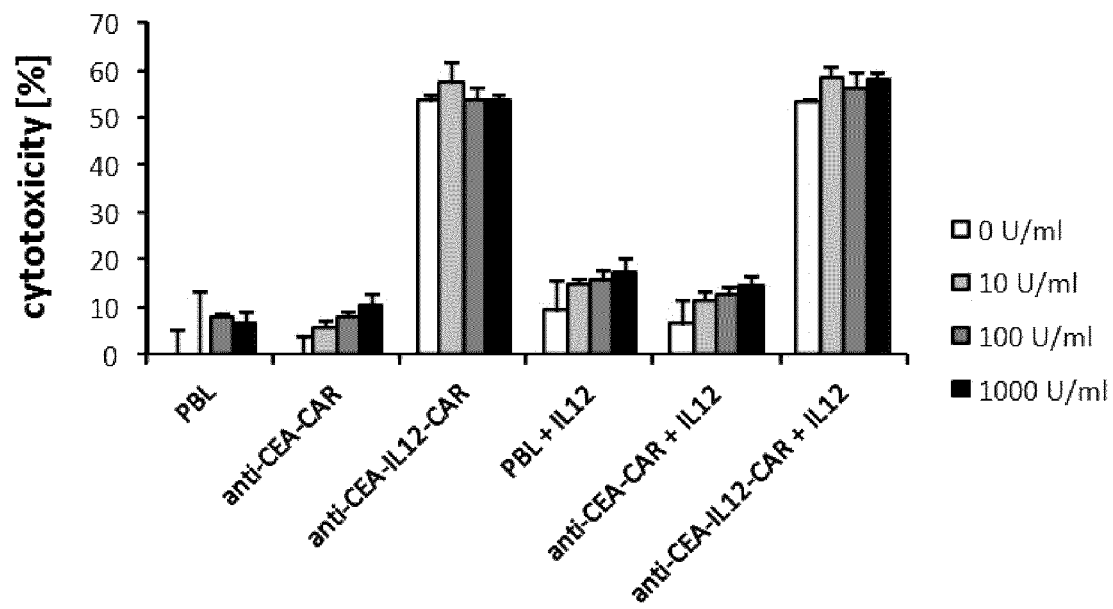

FIG. 8: Combined stimulation by exogenous IL2 and IL12 has no impact on target cell lysis of hybrid anti-CEA-IL12-CAR and conventional anti-CEA-CAR, respectively.

Non-transduced and CAR T cells (2.5×10(4)/well) were co-cultivated for 48 h with CEA+ Skov3 tumor cells (2.5×10(4)/well) in presence of mIL12 (5 ng/ml) or IL2 (10-1000 U/ml) or a combination of both, respectively. After 48 h target cell viability was determined by a colorimetric tetrazolium-salt based XTT assay. Cytotoxicity was calculated by 100−viability [%]. Data represent mean of triplicates+−standard deviation (SD).

Figure 9:
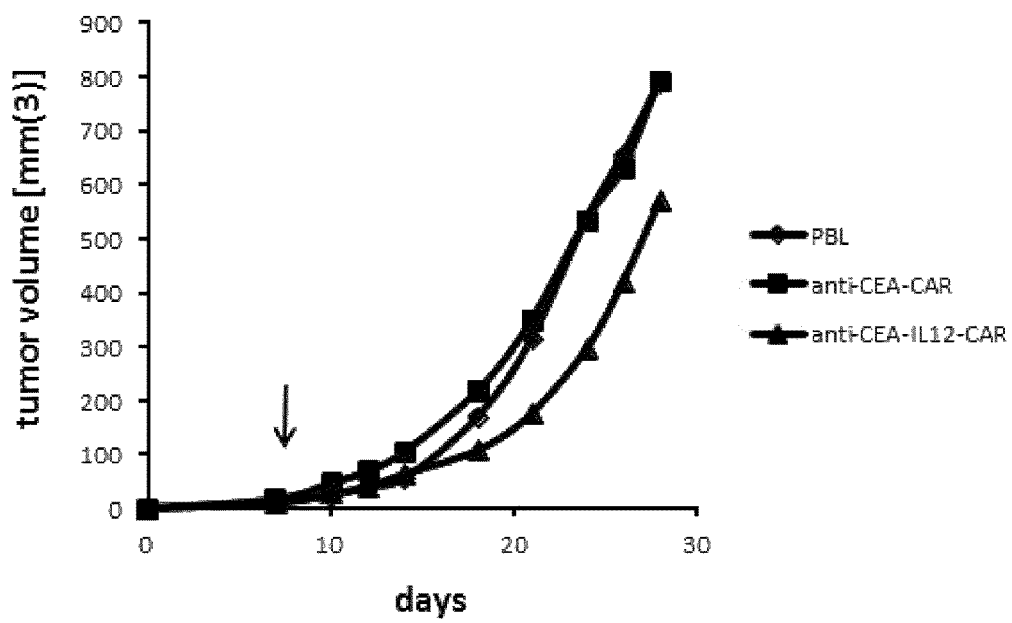

FIG. 9: Anti-CEA-CAR T cells inhibit growth of Skov3 tumors in immune deficient Rag−/− common gamma−/− mice.

Rag−/− common gamma−/− mice were subcutaneously grafted with Skov3 tumor cells (5×10(6)/mouse; 6 animals/group). After establishment of tumors mice received a single intravenous dose of non-transduced or CAR T cells (1×10(7)/mouse). The number of CAR T cells was 14% (anti-CEA-CAR) and 9% (anti-CEA-IL12-CAR), respectively. Data represent mean values. The arrow indicates time of T cell injection.

Figure 10:
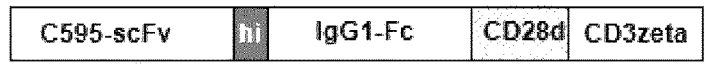
Figure 10:

FIG. 10: Expression cassettes of the anti-Muc1-CAR and the anti-Muc1-IL12-CAR.
(A) Expression cassette of the anti-Muc1 CAR.
(B) Expression cassette of the anti-Muc1 scFv-IL12-CAR.

Figure 11:
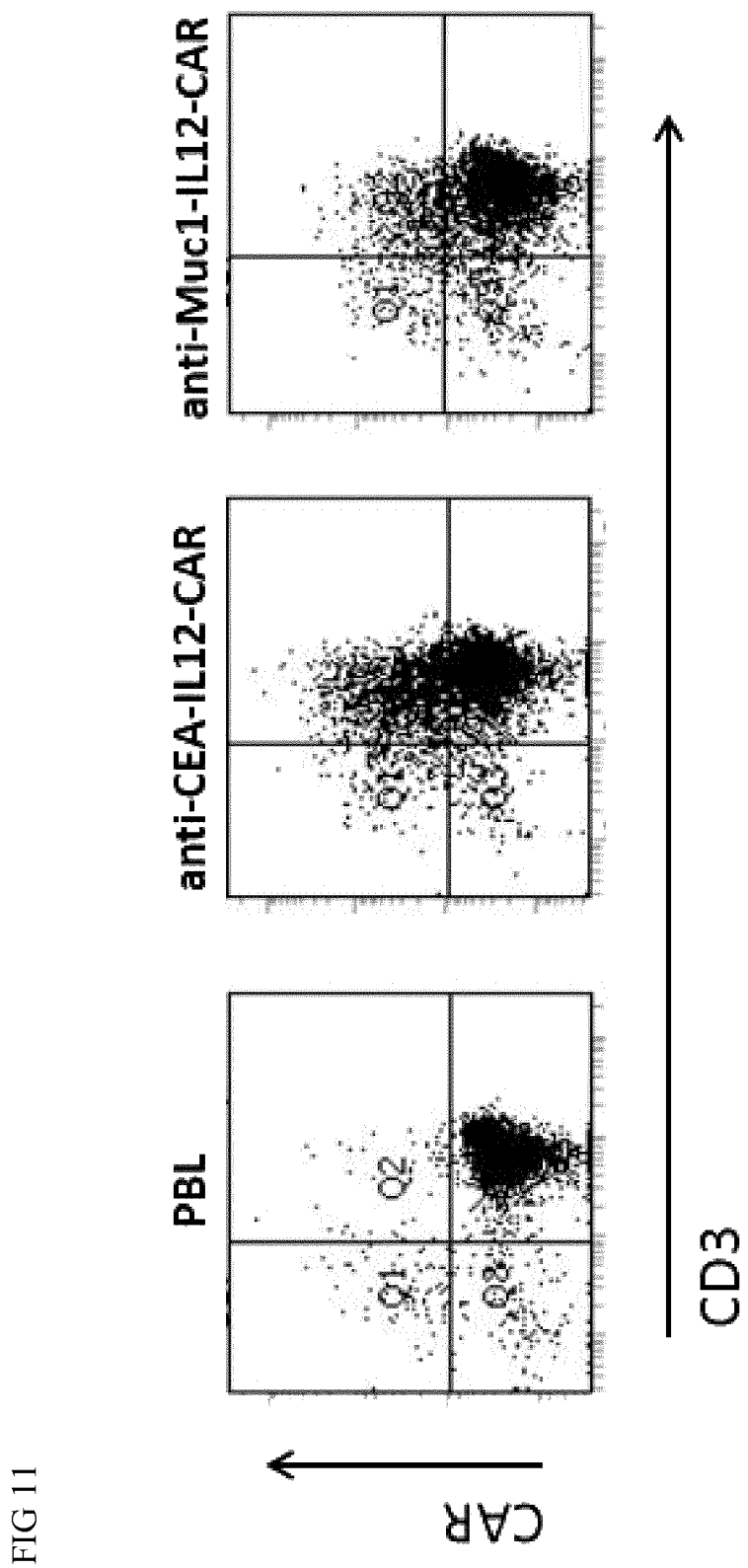

FIG. 11: Expression of the scFv-IL12-CARs with different antigen specificities in peripheral blood T cells.

T cells from the peripheral blood were transduced to express the anti-CEA-IL12-CAR or the anti-Muc1-IL12-CAR, respectively. CARs were detected on the T cell surface by two-color flow cytometry utilizing an anti-human IgG antibody, which detects the extracellular Fc spacer, and an anti-CD3 antibody, respectively. FACS dot plots demonstrate the expression of respective scFv-IL12-CARs on the surface of T cells.

Figure 12:
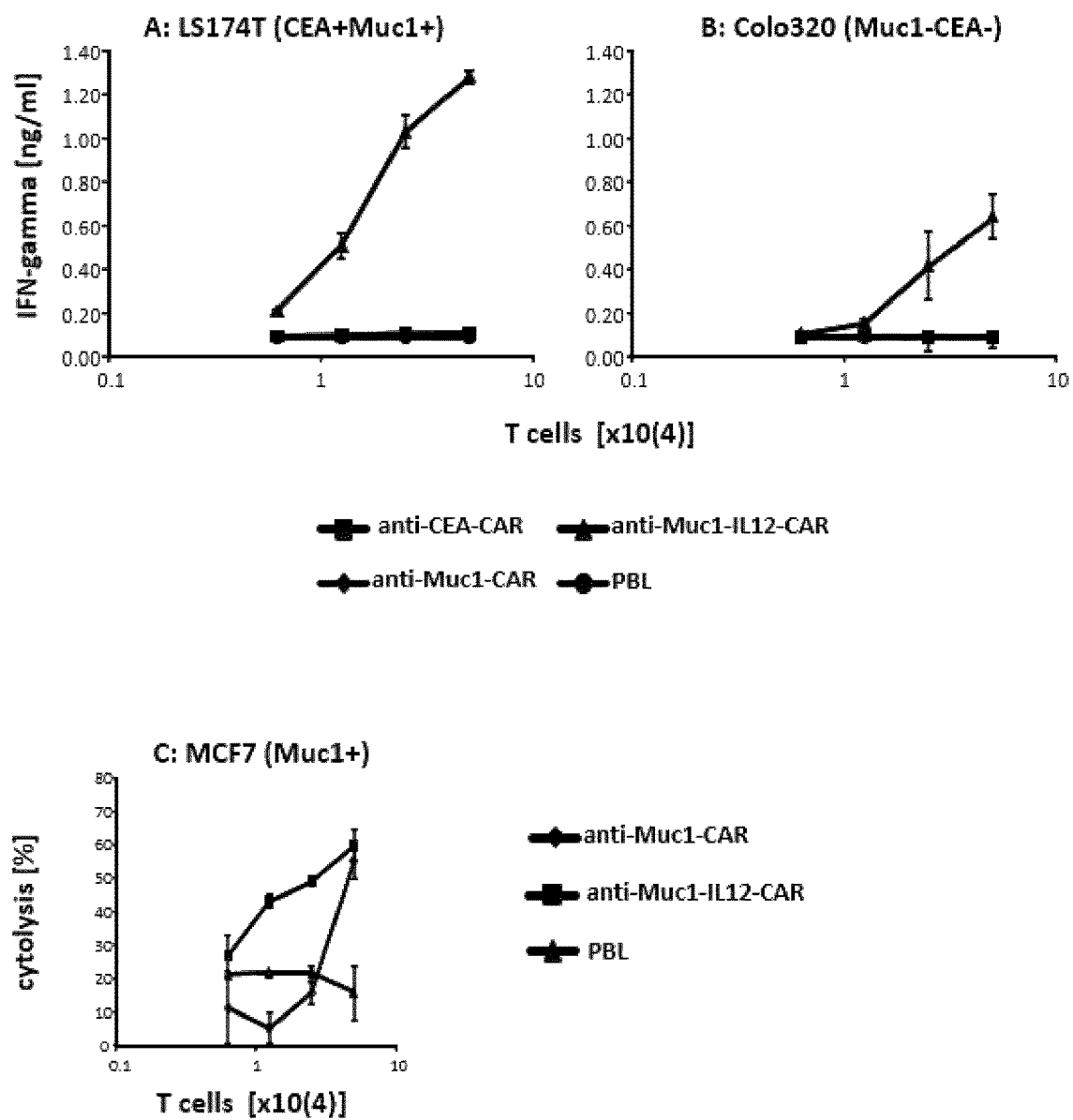

FIG. 12: The anti-Muc1-IL12-CAR enhanced IFN-γ secretion upon antigen engagement.
(A, B) CAR T cells (0.313-2.5×10(4) cells/well) were co-cultivated for 48 h with Muc1+ LS174T and Muc1− Colo320 tumor cells (each 2.5×10(4) cells/well), respectively. After 48 h, supernatants were tested for IFN-γ by ELISA. Data represent means of triplicates+/−standard deviation (SD).
(C) Anti-Muc1-CAR T cells, anti-Muc1-IL12-CAR T cells and non-transduced T cells for control (each 0.313-2.5×10(4) cells/well) were co-cultivated with Muc1+ MCF7 tumor cells (2.5×10(4) cells/well). After 48 h target cell viability was determined by a colorimetric tetrazolium-salt based XTT assay. Cytotoxicity was calculated by 100−viability [%]. Data represent mean of triplicates+/−standard deviation (SD).

Figure 13:
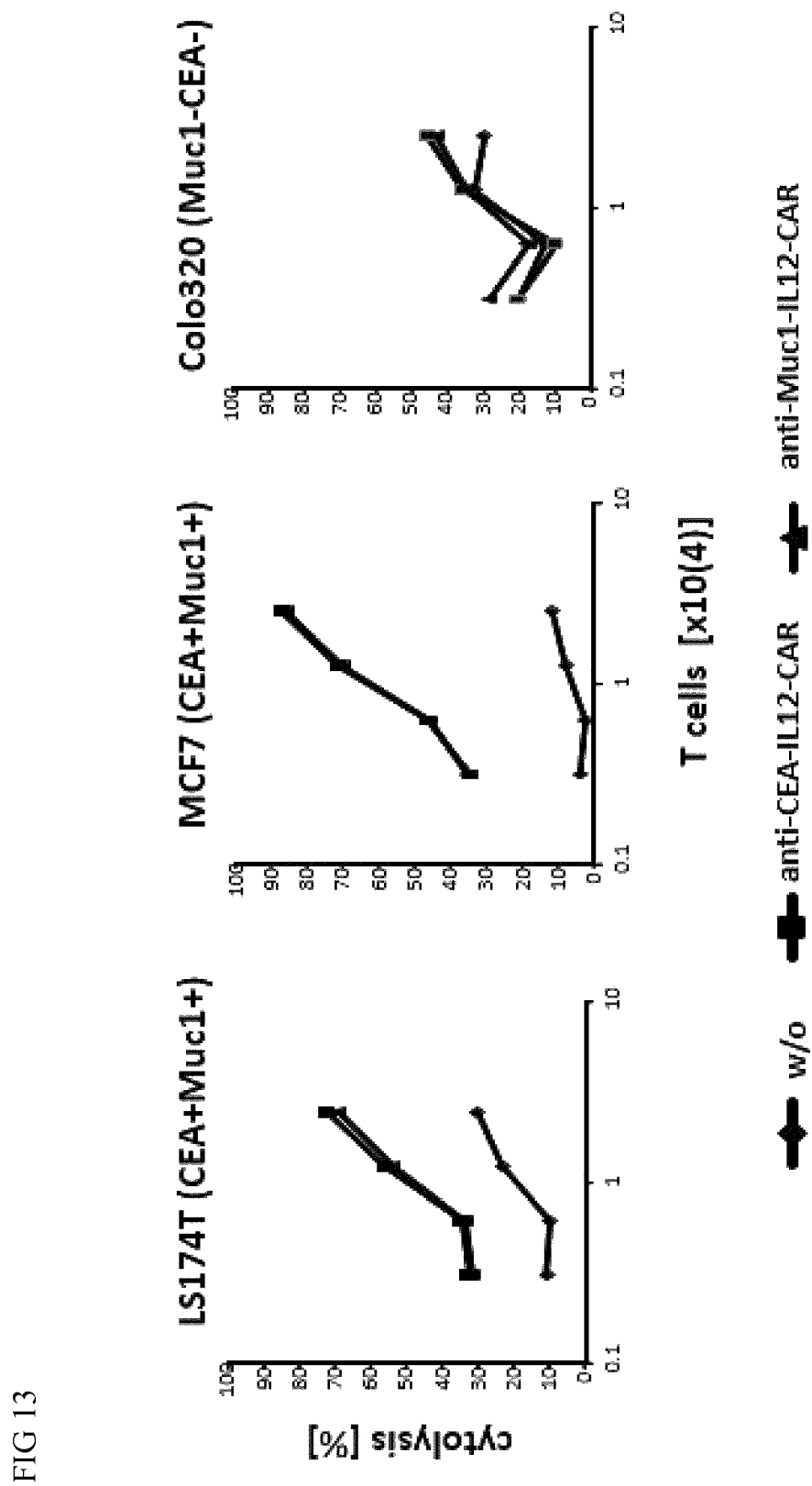

FIG. 13: Anti-CEA-IL12 and anti-Muc1-IL12 CART cells lyse tumor cells specifically with high efficiency.

Anti-Muc1-IL12-CAR, anti-CEA-IL12 CAR T cells and non-transduced T cells for control, respectively, were co-cultivated with CEA+Muc1+ LS174T, CEA+Muc1+ MCF7 or CEA−Muc1− Colo 320 tumor cells (each 2.5×10(4) cells/well). After 48 h target cell viability was determined by a colorimetric tetrazolium-salt based XTT assay. Cytotoxicity was calculated by 100−viability [%]. Data represent mean of triplicates+/−standard deviation (SD). Data demonstrate efficient and specific lysis of target cells by hybrid scFv-IL12-CAR T cells.

Figure 14:
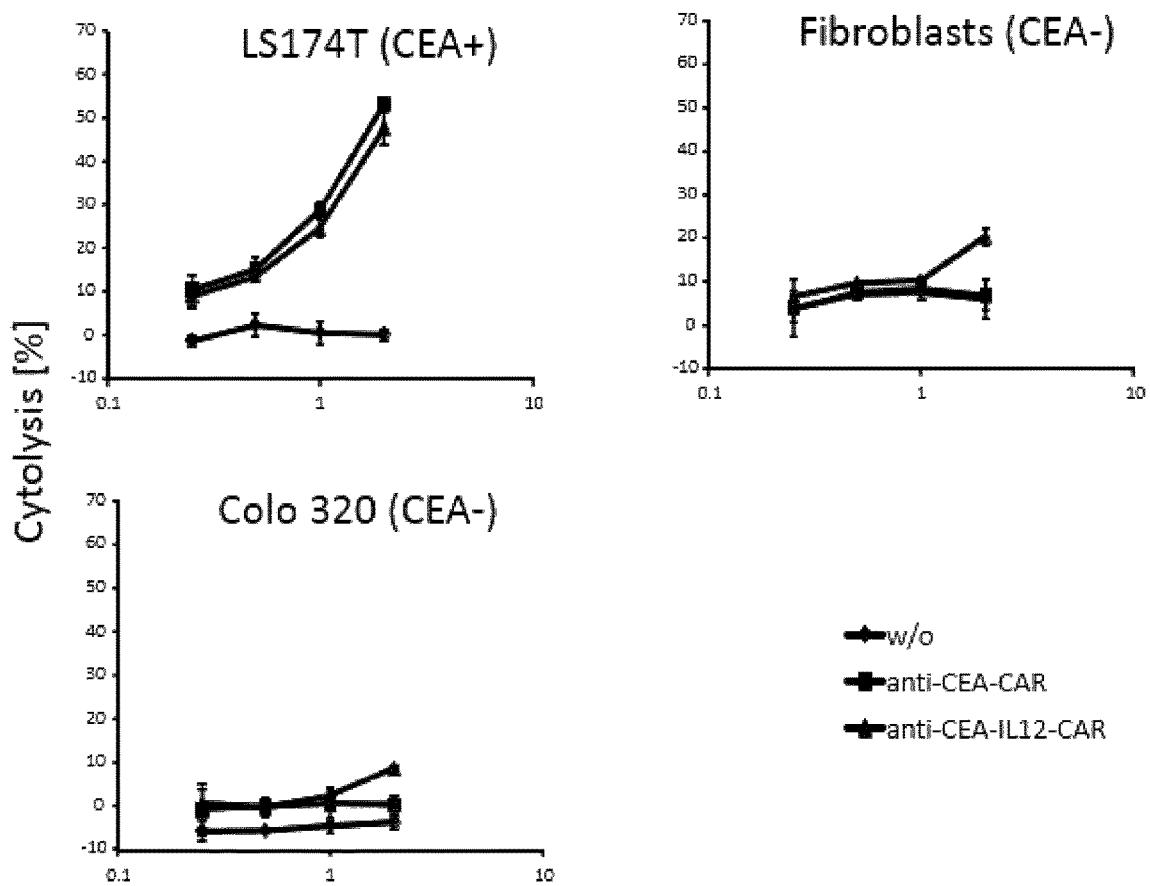

FIG. 14: Anti-CEA-IL12 CAR T cells do not lyse CEA− normal fibroblasts.
(A) Anti-CEA-CAR−, hybrid anti-CEA-IL12-CAR− and non-transduced T cells (each 0.313-2.5×10(4) cells/well) were co-cultivated with CEA+ LS 174T, CEA− normal fibroblasts and CEA− Colo320 tumor cells (each 2.5×10(4) cells/well). After 48 h target cell viability was determined by a colorimetric tetrazolium-salt based XTT assay. Cytotoxicity was calculated by 100−viability [%]. Data represent mean of triplicates+/−standard deviation (SD).

Figure 15:

FIG. 15: Expression cassette of the IL7-anti-CEA-CAR.
The IL7-CAR harbors IL7 instead of IL12 as active cytokine and has the cytokine domain in the terminal position whereas the IL12 CAR in the position between the scFv and the IgG1-Fc spacer. li, linker; hi, hinge; CD28d, CD28 intracellular domain with mutated lck binding site; BW431/26 scFv, anti-CEA scFv.

Figure 16:
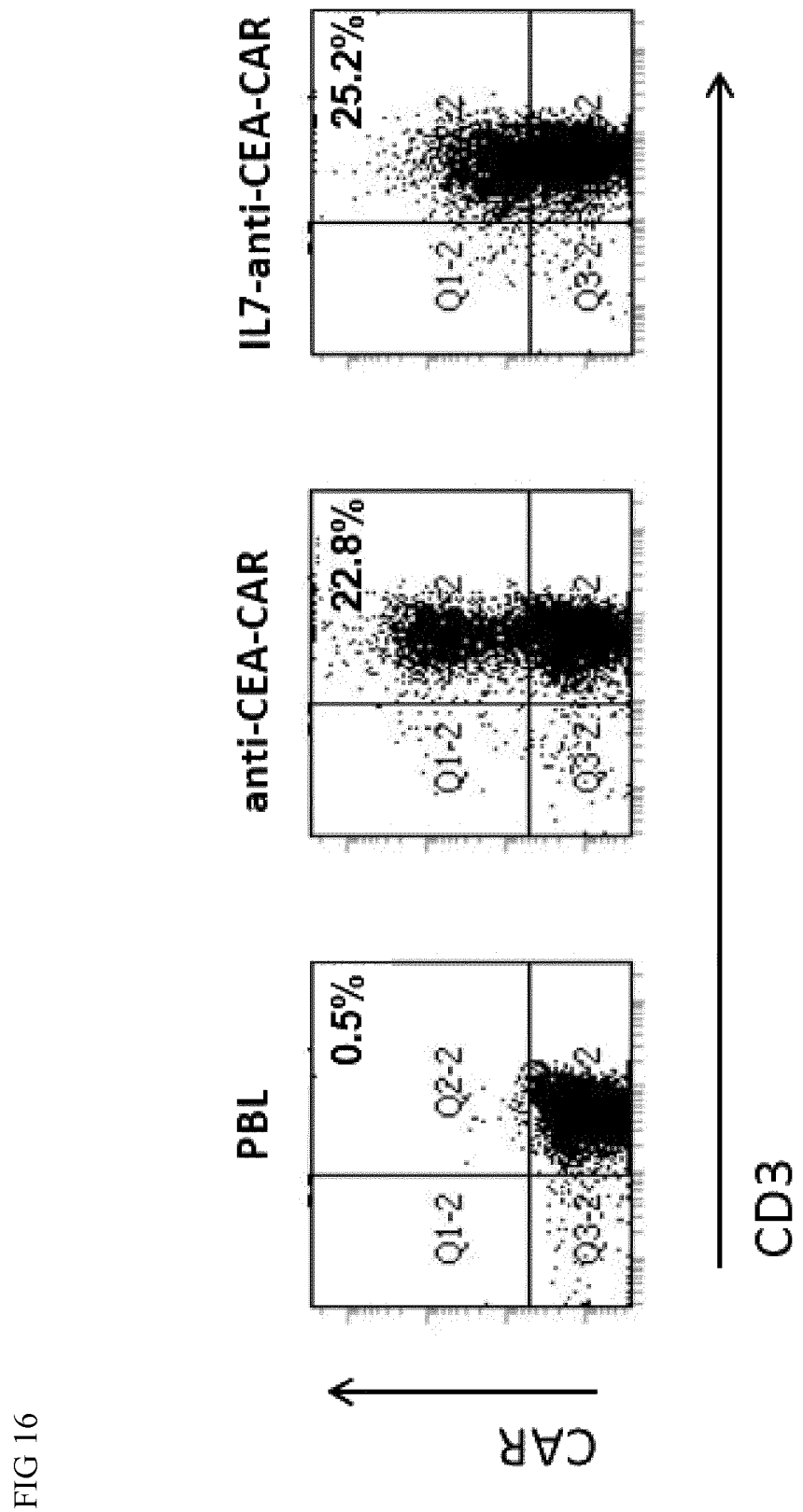

FIG. 16: Expression of hybrid IL7-anti-CEA-CAR in peripheral blood T cells.
T cells of peripheral blood were transduced to express the anti-CEA-CAR or hybrid IL7-anti-CEA-CAR. CARs were detected on the cell surface by two-color flow cytometry utilizing an anti-human IgG and anti-CD3 antibody, respectively. Data demonstrate efficient expression of hybrid IL7-anti-CEA-CAR. w/o, without CAR.

Figure 17:
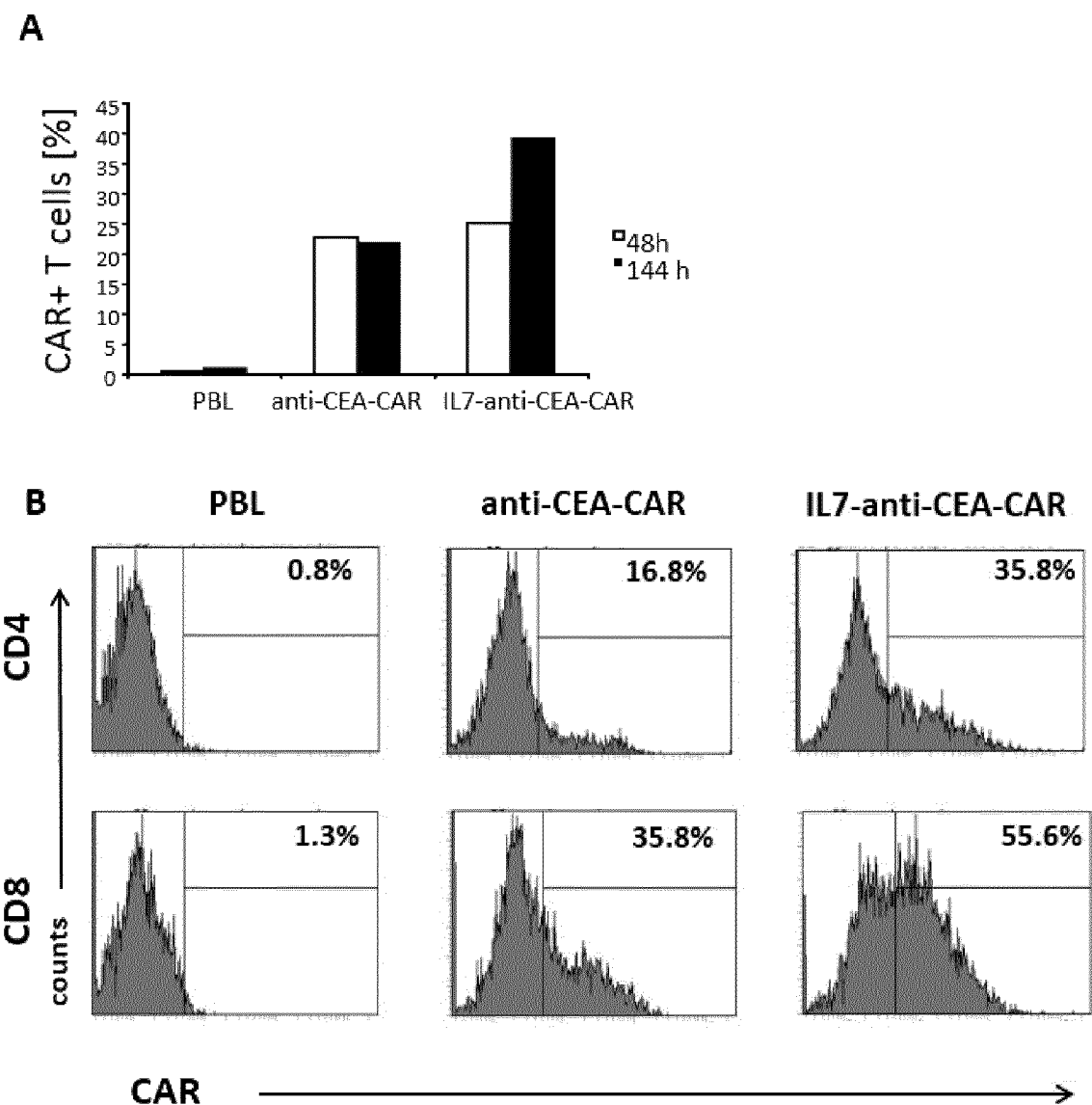

FIG. 17: Preferential expansion of CD8+ T cells with IL7-anti-CEA-CAR.
(A) Peripheral blood T cells were engineered by retroviral transduction with the IL7-anti-CEA CAR and, for comparison with the anti-CEA CAR without cytokine, respectively. T cells were cultivated in the presence of IL2 (500 U/ml). CAR expression was monitored 72 h and 144 h after transduction by two color flow cytometry.
(B) T cells were stained 144 h after transduction with anti-CD4 and anti-CD8 antibodies for T cell classification and with an anti-human IgG Fc antibody to record the CAR. Cells were analyzed by flow cytometry and the number of CAR+ T cells was determined.

Figure 18:
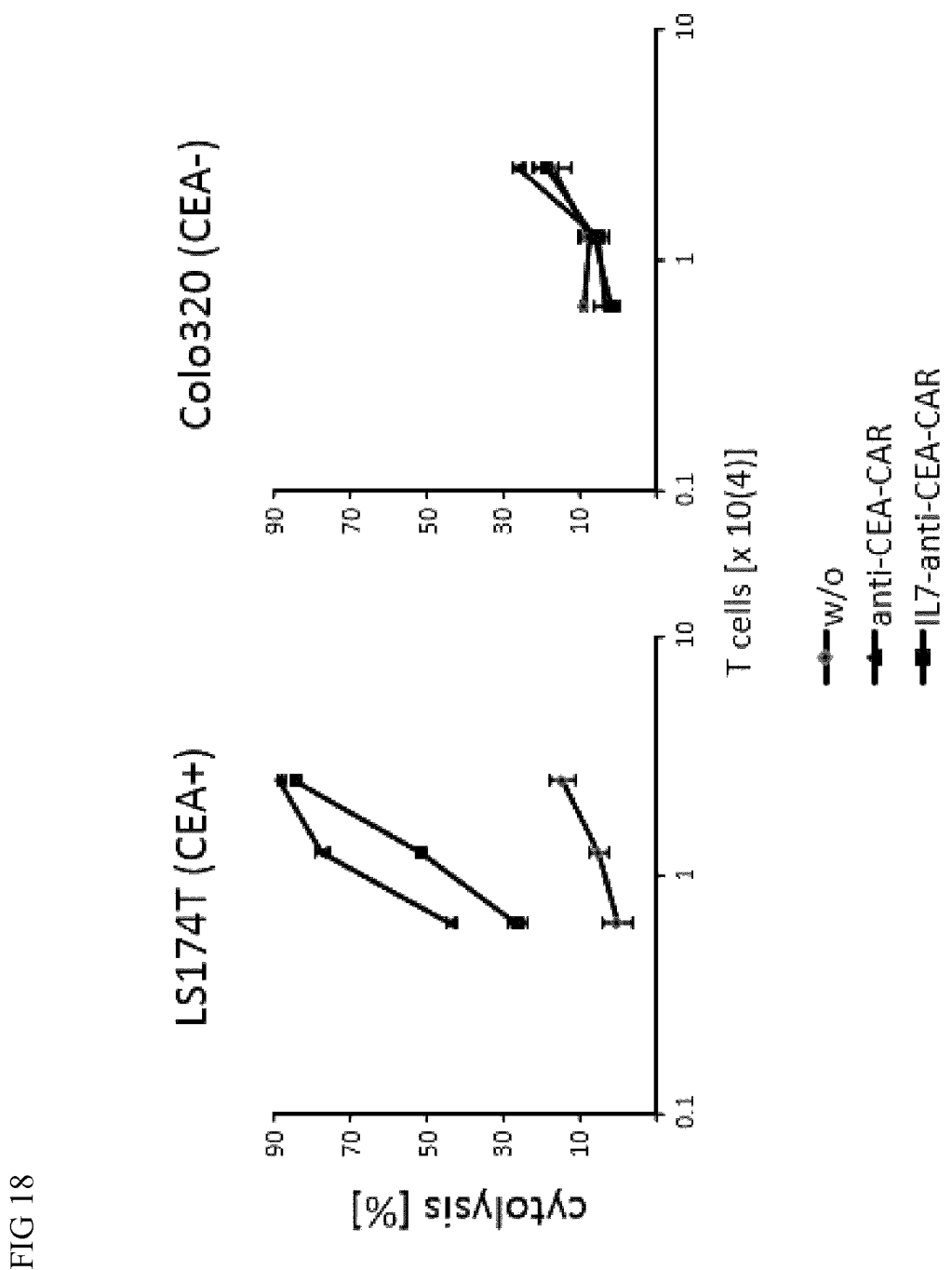

FIG. 18: IL7-anti-CEA-CAR T cells lyse CEA+ tumor cells with high efficiency.
Anti-CEA-CAR, IL7-anti-CEA-CAR- and non-transduced T cells (each 0.625-5×10(4) cells/well) were co-cultivated with CEA+LS174T or CEA− Colo320 tumor cells (each 2.5×10(4) cells/well). After 48 h target cell viability was determined by a colorimetric tetrazolium-salt based XTT assay. Cytotoxicity was calculated by 100−viability [%]. Data represent mean of triplicates+/−standard deviation (SD). w/o, without CAR.

DETAILED DESCRIPTION OF THE INVENTION

In a first aspect the invention provides a chimeric antigen receptor (CAR), comprising an extracellular part, at least one intracellular signaling domain, and at least one transmembrane domain, wherein the extracellular part of said CAR comprises
 a) at least one antigen binding domain, and
 b) at least one cytokine receptor activating or blocking domain.

The at least one intracellular signaling domain may comprise at least one co-stimulatory domain and/or at least one primary signaling domain.

The CAR may comprise, from the N-terminus to the C-terminus the extracellular part comprising at least one antigen binding domain and at least one cytokine receptor activating or blocking domain, the transmembrane domain, and the at least one intracellular signaling domain. The CAR may also comprise two or more members of polypeptides which together work as functional active CAR (e.g., switch-on CAR, switch-off CAR, conditionally active CAR, regulatable CAR, controllable CAR, multi-chain CAR), e.g. a first polypeptide comprising at least one antigen binding domain, at least one cytokine receptor activating or blocking domain, a first member of a dimerization pair, and a transmembrane domain; and a second polypeptide comprising a second member of a dimerization pair, and at least one intracellular signaling domain (for the key signaling of the active CAR), and optionally a transmembrane domain, wherein the CAR is activated upon dimerization by a dimerizer recognizing the members of the dimerization pair. Such CAR constructs with split key signaling and recognition modules are disclosed e.g. in WO2014/127261A1, WO2015017214A1, WO2015090229A1, WO2015142661A1, and WO2015150771A1.

In one embodiment of the invention said at least one cytokine receptor activating domain of said CAR may be selected from the group consisting of IL-1, IL-2, IL-4, 11-5, IFN-gamma, IL-6, IL-7, GM-CSF, p40-p35 variant of IL-12, IL-17, IL-18, IL-23, IL-32, TNF-alpha or functional fragments thereof. Said cytokine receptor activating domains may have an amino acid sequence identity of at least 85%, 90%, 95%, 96%, 97%, 98%, 99% or 100% compared with the wild type sequence of said cytokine receptor activating domains, respectively.

In one embodiment of the invention said at least one cytokine receptor blocking domain of said CAR may be selected from the group consisting of TGF-beta, IL-10, p40-p40 variant of IL12, IL-13, IL-32 or functional fragments thereof. Said cytokine receptor blocking domains may have an amino acid sequence identity of at least 85%, 90%, 95%, 96%, 97%, 98%, 99% or 100% compared with the wild type sequence of said cytokine receptor blocking domains, respectively. In one embodiment of the invention said at least one cytokine receptor activating or blocking domain of said CAR activates or blocks the interleukin 12 receptor.

The interleukin 12 receptor may be activated or blocked/inhibited by any molecule or peptide sequence which can interact with and thereby activates or blocks/inhibits said receptor. Preferentially, said at least one cytokine receptor activating domain is the cytokine IL-12 or a domain functional fragment thereof, more preferentially, said at least one cytokine receptor activating domain is the single chain p40-p35 IL-12, or an amino acid sequence with 85%, 90%, 95%, 96%, 97%, 98%, or 99% identity thereof.

In one embodiment of the invention said at least one cytokine receptor activating domain comprises the sequence encoded by SEQ ID NO:1 or a sequence with 85%, 90%, 95%, 96%, 97%, 98% or 99% identity thereof.

In one embodiment of the invention said at least one cytokine receptor activating or blocking domain of said CAR activates or blocks the interleukin 7 receptor.

The interleukin 7 receptor may be activated or blocked/inhibited by any molecule or peptide sequence which can interact with and thereby activates or blocks/inhibits said receptor. Preferentially, said at least one cytokine receptor activating domain is the cytokine IL-7 or a functional fragment thereof or an amino acid sequence with 85%, 90%, 95%, 96%, 97%, 98% or 99% identity thereof.

In one embodiment of the invention said at least one cytokine receptor activating domain comprises the sequence encoded by SEQ ID NO:14 or a sequence with 85%, 90%, 95%, 96%, 97%, 98% or 99% identity thereof.

In one embodiment of the invention said at least one cytokine receptor activating or blocking domain is between the at least one antigen binding domain and the at least one transmembrane domain of said CAR. In another embodiment said at least one cytokine receptor activating or blocking domain is flanked by linker domains, e.g. the IgG1 hinge.

In a further embodiment of the invention said at least one cytokine receptor activating or blocking domain is at the N-terminal position of the amino acid sequence of said CAR, i.e. the at least one antigen binding domain is between the at least one cytokine receptor activating or blocking domain and the at least one transmembrane domain of said CAR.

The activation of the receptors corresponding to the respective cytokine receptor activating or blocking domain, e.g. the activation of the IL-12 receptor or IL-7 receptor as described herein, result in the increased release of IFN-γ and other improved effector functions well-known to the skilled person by the cell harboring said receptor. The effect of activation or inhibition of said receptor is independent from the extracellular position of said at least one cytokine receptor activating or blocking domain of the CAR as disclosed herein.

In one embodiment of the invention said at least one antigen binding domain comprises at least one single chain variable fragment of an antibody that binds to the antigen, or at least one heavy or light chain variable region of an antibody that binds to the antigen.

In one embodiment of the invention the at least one antigen of said at least antigen binding domain is a tumor-specific antigen or tumor-associated antigen.

In one embodiment of the invention the at least one antigen of said at least one antigen binding domain is carcinoembryonic antigen (CEA).

In one embodiment of the invention said antigen binding domain comprises an anti-CEA scFV antigen binding domain, or an amino acid sequence with 85%, 90%, 95%, 96%, 97%, 98% or 99% identity thereof.

In one embodiment of the invention said intracellular signaling domain comprises a CD3 zeta signaling domain.

In one embodiment of the invention said at least one co-stimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof. In one embodiment of the invention said CAR comprises the amino acid sequence encoded by SEQ ID NO:2, or an amino acid sequence with 85%, 90%, 95%, 96%, 97%, 98% or 99% identity thereof.

In one embodiment of the invention the CAR is an anti-CEA-IL12-CAR comprising the sequence of SEQ ID NO:3 or the sequence encoded by SEQ ID NO:4.

In one embodiment of the invention the CAR is an IL7-anti-CEA-CAR comprising the sequence of SEQ ID NO:13 or the sequence encoded by SEQ ID NO:12.

In one embodiment of the invention the at least one antigen of said at least one antigen binding domain is Mucin-1 (Muc1, CD227).

In one embodiment of the invention said antigen binding domain comprises an anti-Muc1 scFV antigen binding domain, or an amino acid sequence with 85%, 90%, 95%, 96%, 97%, 98% or 99% identity thereof.

In one embodiment of the invention the CAR is an anti-Muc1-IL12-CAR comprising the sequence of SEQ ID NO:6 or the sequence encoded by SEQ ID NO:5.

In one embodiment of the invention said CAR is for use in immunotherapy, i.e. for use of treatment of a disease in a subject.

In one embodiment of the invention said CAR is for use of treatment of cancer in a subject.

The cancer includes, inter alia, hematological malignancies such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma, or solid cancer like carcinoma of the gastrointestinal tract, mammary gland, ovary, prostate, liver, lung, kidney, or a combination thereof.

In one embodiment of the invention said CAR is for use of treatment of autoimmune diseases, chronic inflammation and/or infection.

In one aspect the invention provides one or more isolated nucleic acid molecule(s) wherein said nucleic acid molecule(s) encode(s) for a CAR, comprising an extracellular part, at least one intracellular signaling domain, and at least one transmembrane domain, wherein the extracellular part of said CAR comprises
  a) at least one antigen binding domain, and
  b) at least one cytokine receptor activating or blocking domain.

The nucleic acids molecule(s) may be constructed so that they encode at least all embodiments of the CARs disclosed herein. There may be a contiguous nucleic acid molecule when all domains of the CAR encoded by said molecule are within one polypeptide. Alternatively, there may be two or more nucleic acid molecules e.g. when some domains of the CAR encoded by said molecules are on separate polypeptides.

In one embodiment of the invention, the nucleic acid molecule(s) encoding the disclosed CARs may be contained in a vector, such as a viral vector. The vector(s) may be DNA vector(s), RNA vector(s), plasmid vector(s), cosmid vector(s), herpes virus vector(s), measles virus vector(s), lentivirus vector(s), adenoviral vector(s), or retrovirus vector(s), or combination(s) thereof.

In certain embodiments of the invention, the vector(s) further comprise(s) a promoter wherein the promoter is an inducible promoter, a tissue specific promoter, a constitutive promoter, a suicide promoter or any combination thereof.

In a further embodiment, the vector(s) expressing the CAR may be further modified to include operative elements to control the expression of CAR cells, or to eliminate CAR cells via a suicide switch (e.g. an apoptosis inducing signaling cascade or a drug that induces cell death).

In another aspect the invention provides a cell comprising one or more isolated nucleic acid molecule(s) wherein said nucleic acid molecule(s) encode(s) for a CAR, comprising an extracellular part, at least one intracellular signaling domain, and at least one transmembrane domain, wherein the extracellular part of said CAR comprises
  a) at least one antigen binding domain, and
  b) at least one cytokine receptor activating or blocking domain.
Said cell may be an immune cell.

Preferentially said cell is a NK cell or T cell, in particular a CD4+ or CD8+ T cell.

In further aspect the invention provides a cell expressing a CAR, comprising an extracellular part, at least one intracellular signaling domain, and at least one transmembrane domain, wherein the extracellular part of said CAR comprises
  a) at least one antigen binding domain, and
  b) at least one cytokine receptor activating or blocking domain.
Said cell may be an immune cell.

Preferentially said cell is a NK cell or T cell, in particular a CD4+ or CD8+ T cell.

In one aspect the invention provides a pharmaceutical composition comprising a population of cells (a cell composition) expressing a CAR comprising an extracellular part, at least one intracellular signaling domain, and at least one transmembrane domain, wherein the extracellular part of said CAR comprises
  a) at least one antigen binding domain, and
  b) at least one cytokine receptor activating or blocking domain.
Said population of cells may be immune effector cells.

Preferentially said population of cells is a population of NK cells and T cells, in particular CD4+ or CD8+ T cell.

Said pharmaceutical composition may comprise an anti-tumor effective amount of a population of said cells.

Said pharmaceutical composition may also comprise a pharmaceutical acceptable carrier.

In one aspect the invention provides a method for treating or preventing a disease in a subject, e.g. cancer, autoimmune diseases, chronic inflammation or infection by administering to the subject the nucleic acid molecule(s) encoding the CAR or cells expressing the CAR of the invention.

Adoptive cell therapy uses immune cell-based, preferentially T cell-based, cytotoxic responses to attack diseased cells, e.g. cancer cells. Immune cells, preferentially T cells, with a natural or genetically engineered reactivity to a patient's cancer are engineered in vitro with the CAR of invention and transferred to the cancer patient. The CAR provides the targeting specificity for cancer. The CAR of the invention can be engineered to comprise an extracellular part comprising an antigen binding domain and a cytokine receptor activating or blocking domain, a transmembrane domain, and an intracellular signaling domain, frequently, e.g. CD3 zeta. The key signaling and antigen recognition modules may be either on one or two (or even more) polypeptides. Splitting the signaling and antigen recognition modules enables for a small molecule-dependent, titratable and reversible control over CAR cell expression (Wu et al, 2015, Science 350: 293-303) due to small molecule-dependent heterodimerizing domains in each polypeptide of the CAR.

Engineered immune cells, preferentially T cells of the invention express a CAR of the invention which is able to recognize and subsequent active or block a cytokine receptor on the same cell or on adjacent other immune cells or on the target cells due to the integration of a cytokine receptor activating or blocking domain into the CAR. The CAR construct of the invention has the effect to locally bind to and activate or block cytokine receptors in addition to binding of the antigen binding domain of the CAR to the antigen of the target cell, wherein mostly the antigen is a tumor associated antigen. The activation of the cytokine receptor by the cytokine receptor activating domain results for example in an altered release of immune modulating substances from the cell into the locally restricted environment. Exemplary, binding to a IL-12 receptor by a CAR-cell harboring an IL-12 receptor activating domain results in an increase of IFN-γ release to said locally restricted environment. The CAR cell attack then benefits from the increasing IFN-γ release with improved cancer cell killing and tumor elimination. Simultaneously severe side effects due to IL-12 mediated toxicity are avoided since no soluble IL-12 is released into the environment.

Exemplary the concept of the invention is shown with a CEA-CAR, i.e. a CAR which has an antigen binding domain against carcinoembryonic antigen (CEA, CD66e) and a IL-12 sequence as cytokine activating domain (see FIG. 1B) or a IL7 sequence as cytokine activating domain (see FIG. 15), whereby the positions of the both cytokine domains are different with regard to their extracellular localization in the CAR. A further CAR with a different specificity for the target cell (anti-Muc1 instead of anti-CEA) was exemplary used to demonstrate the independence of the concept of the invention from the antigen of the target cell that is recognized by the CAR. Therefore, no limitation to the CARs specifically used herein harboring said specific antigen binding domains and said specific cytokine receptor activating domains is intended as the concept can be transferred to other CARs harboring other antigen binding domains and other cytokine receptor activating or blocking domains.

The CAR with the CEA antigen binding domain and the IL-12 receptor activating domain (hereafter "CEA-CAR with IL-12 module" or "anti-CEA-IL12-CAR") redirects T cells in a specific fashion as indicated by specific killing (FIG. 6) and IFN-gamma release (FIG. 5) upon incubation with CEA$^+$ cancer cells but not with CEA$^-$ cancer cells.

Figure 6:
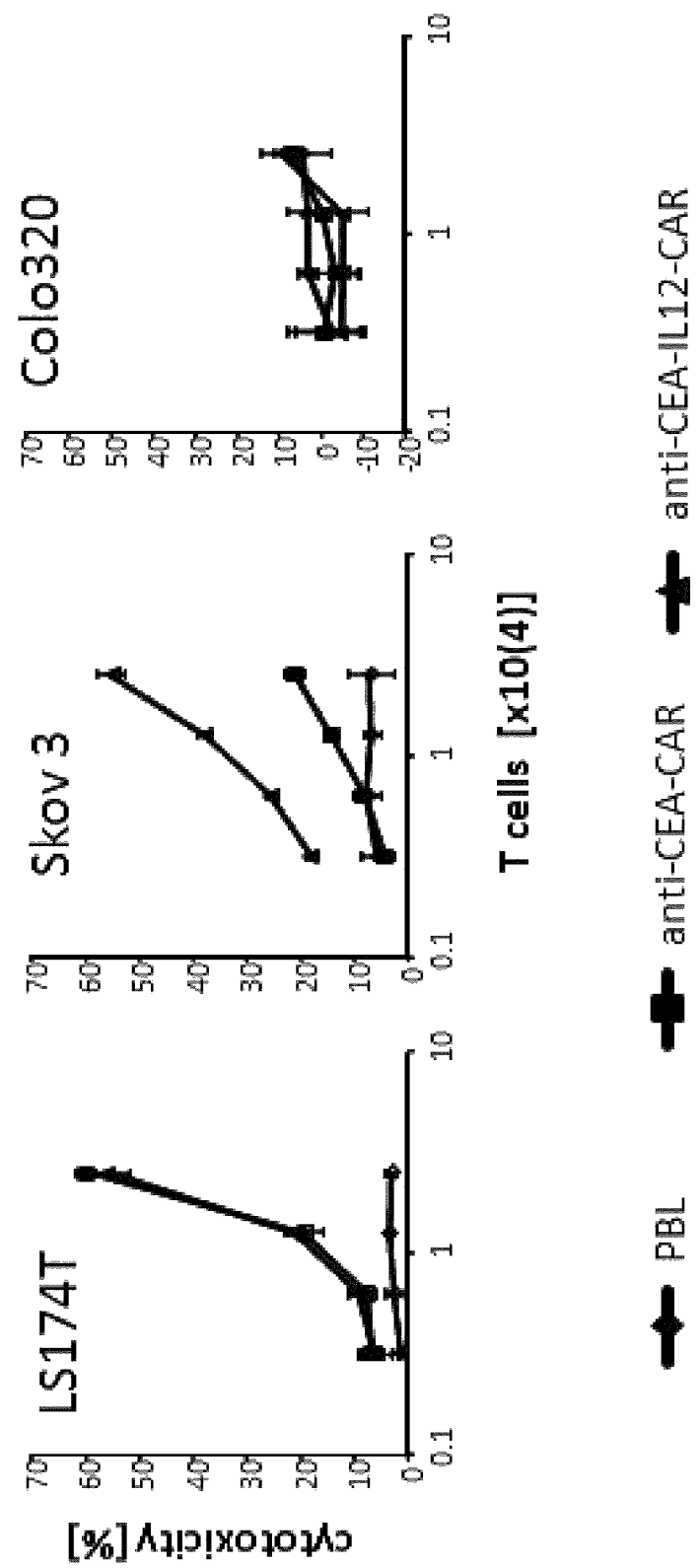
FIG. 6: CAR-mediated target cell lysis.
CAR T cells (0.313-2.5×10(4)/well) were co-cultivated for 48 h with CEA+ LS174T or Skov3 tumor cells and for control with CEA− Colo320 tumor cells (each 2.5×10(4)/well), respectively. After 48 h target cell viability was determined by a colorimetric tetrazolium-salt based XTT assay. Cytotoxicity was calculated by 100−viability [%]. Data represent mean of triplicates+−standard deviation (SD).

Some cancer cells suppress the T cell activation by various means with the result that the T cell anti-tumor response is not successful. This is also the case for TCR or CAR redirected T cells. Using a CEA-CAR with IL-12 module for targeting, engineered T cells are successfully activated and mediate a productive anti-cancer cell response which is not obtained with T cells with the CEA specific CAR without IL-12 module. SKOV-3 cells are ovarian adenocarcinoma cells which are frequently used as a model for cancer induced inhibition of IL-2 dependent signaling pathways in T cells. SKOV-3 cells suppress the induction of the IL-1receptor β- and γ-chains, the signaling through the JAK-STAT5 pathway, reduce the IFN-γ and increase the IL-10 levels and inhibit the cell cycle by G0/G1 arrest. Consequently, in a long-term assay, killing by CAR T cells is poor compared to killing of other cancer cell lines by the same CAR T cells. However, the specific killing of SKOV-3 cells is substantially improved upon adding the IL-12 module into the CAR compared to the killing by CART cells which lack the IL-12 module (FIG. 6).

A number of mouse models indicate that CEA target antigen recognition and specific T cell activation is mediated by the CEA specific CAR in vivo. Therefore it is expected that the same binding and activation occurs through the CEA-CAR with the IL-12 module. Moreover, any other cytokine receptor activating or blocking domain likely acts in the predictive fashion in vivo.

In one embodiment of the invention a DNA construct (vector, plasmid) is generated encoding for a CAR as disclosed herein, e.g. for a CEA-CAR with IL-12 module. The construction of such expression vectors can be performed by recombinant methods well known in the art. Alternatively, the nucleic acid sequences can be produced synthetically.

The DNA or RNA construct (nucleic acid molecule(s)) encoding the CAR of the invention can be transfected or transduced into a host cell by methods well known in the art (e.g. viral-based systems, physical methods, biological methods, chemical methods). Regardless the methods used to integrate, preferentially stably integrate, the DNA encoding the CAR of the invention, in the host cell, as a result the host cell expresses a CAR which harbors a cytokine receptor activating or blocking domain in its extracellular part.

In one embodiment of the invention the CAR which harbors a cytokine receptor activating or blocking domain in its extracellular part is expressed in immune cells or immune cell subsets.

In one embodiment of the invention the CAR which harbors a cytokine receptor activating or blocking domain in its extracellular part is expressed in T cells or T cell subsets.

In one embodiment of the invention the CAR which harbors a cytokine receptor activating or blocking domain in its extracellular part is expressed in NK cells or NK cell subsets.

In one embodiment of the invention an engineered cell expressing a CAR which harbors a cytokine receptor activating or blocking domain in its extracellular part is isolated (enriched or separated) after the transfection/transduction process for generating such an engineered CAR cell from non-transfected/transduced cells by methods well known in the art, e.g. fluorescent based separating technologies such as FACS® or magnetic cell separation methods such as MACS®.

Generally, the immune cells, preferentially T cells for generating engineered cells expressing the CAR of the invention may be obtained from a subject Immune cells, preferentially T cells, can be obtained from a variety of sources such as peripheral blood mononuclear cells (PMBCs), bone marrow, lymph node tissue, cord blood or thymus tissue. For enrichment of these cells methods well known in the art can be used such as centrifugation through a Ficoll™ or PERCOLL™ gradient or positive/negative selection techniques such as fluorescent sorting (e.g. FCAS-sort) or magnetic sorting (e.g. MACS®).

Exemplary, T cells of a blood sample of a subject are magnetically labelled, for example with a magnetic bead coupled to antibodies specific for CD4 and for CD8, respectively, washed, magnetically enriched and collected. Then these T cells may be engineered to express the CAR which harbors a cytokine receptor activating or blocking domain in its extracellular part on their cell surface.

In one embodiment of the invention the isolated/enriched engineered T cells expressing the CAR which harbors a cytokine receptor activating or blocking domain in its extracellular part prior or after genetic modification can be activated and expanded to increase the number of engineered T cells using methods well known in the art, for example polyclonal stimulation with anti-CD3/anti-CD28 beads or TransAct T Cell Reagents (Miltenyi Biotec; EP2711418A1). Preferentially, said number of engineered T cells is increased to a therapeutically effective amount.

In one embodiment of the invention a cell expressing the CAR of the invention is engineered by a RNA encoding the CAR of the invention. The RNA can be transfected or transduced into a host cell by methods well known in the art (e.g. viral-based systems, physical methods, biological methods, chemical methods). In general, such an "RNA-engineered cell" is disclosed in detail in WO2013/040557. Regardless the methods used to transfer the RNA encoding the CAR of the invention into the host cell, as a result the host cell expresses a CAR which harbors a cytokine receptor activating or blocking domain in its extracellular part. "RNA-engineered cells" express the CAR for a limited time (transient expression).

In one embodiment of the invention the genetically modified cells expressing the CAR which harbors a cytokine receptor activating or blocking domain in its extracellular part, preferentially T cells, are generated in an automated process in a closed system. A process for the generation of genetically modified cells, preferentially T cells, comprises e.g. the steps:
a) providing a cell sample
b) preparation of the cell sample by centrifugation
c) magnetic separation of the cells, preferentially T cells,
d) activation of the enriched cells, preferentially T cells, using modulatory agents
e) genetically modifying the cells, preferentially T cells, to express the CAR of the invention
f) expansion of the genetically modified cells, preferentially T cells, in a cultivation chamber
g) washing of the cultured cells, preferentially T cells.

All these steps may be performed in a closed system, preferentially in a closed and sterile system. The process is especially suited for preparing gene modified cells, preferentially T cells, wherein the enriched cells, preferentially T cells, are gene modified by using viral and/or non-viral vectors. Any of these steps may be multiplied, omitted or may occur in a different order.

The modulatory agents may be selected from agonistic antibodies and/or cytokines.

The gene-modified cells, preferentially T cells, may be enriched by magnetic labelling of cells and magnetic separation before or after cultivation to obtain higher frequency of gene-modified cells, preferentially T cells, in the final cellular product.

As closed and sterile system for cell modification, the fully automated cell processing device CliniMACS Prodigy® and associated tubing sets (Miltenyi Biotec GmbH, Germany) may be used (WO2009/072003). This closed system meets the requirements of GMP-grade processing of almost any kind of cellular products and may allow reducing clean room requirements, improve technology transfer and harmonization of cell manufacturing processes.

In one embodiment of the invention the CAR which harbors a cytokine receptor activating or blocking domain in its extracellular part is used for the treatment in a subject having a disease, disorder or condition associated with an antigen which can specifically be bound by the antigen binding domain of the CAR of the invention.

In one embodiment of the invention the CAR of the invention is for use in the treatment of cancer in a subject suffering from cancer. Immune cells, e.g. T cells of a subject, are isolated or established immune cell lines are used. The subject may suffer from said cancer or may be a healthy subject. These cells are genetically modified in vitro to express the CAR of the invention. These engineered cells may be activated and expanded in vitro. In cellular therapy these engineered cells are infused to a recipient in need thereof. These cells may be a pharmaceutical composition. The infused cells in the recipient may be able to kill (or at least stop growth of) cancerous cells expressing the antigen which is recognized by the antigen binding domain of the CAR of the invention. The recipient may be the same subject from which the cells were obtained (autologous cell therapy) or may be from another subject of the same species (allogeneic cell therapy).

In one embodiment of the invention the subject suffering from cancer may be treated with the pharmaceutical composition of the invention together with an immune modulatory agent, such as but not limited to Rapamycin or cell activation checkpoint targeting drugs.

In one embodiment of the invention the subject may be treated additionally (simultaneously or subsequently) with classic chemotherapy. Classic chemotherapeutic agents suited to treat cancers are well known in the art.

The immune cells, preferentially T cells engineered to express a CAR which harbors a cytokine receptor activating domain in its extracellular part may be administered either alone, or as a pharmaceutical composition in combination with diluents and/or with other components or cell populations. Briefly, pharmaceutical compositions of the present invention may comprise a cell population of genetically modified cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions (population of cells) to the subject may be carried out in any convenient manner known in the art.

Pharmaceutical compositions of the present invention may be administered in a manner appropriate to the disease to be treated. Appropriate dosages may be determined by clinical trials. But the quantity and frequency of administration will also be determined and influenced by such factors as the condition of the patient, and the type and severity of the patient's disease.

A pharmaceutical composition comprising the immune cells, preferentially T cells disclosed herein may be administered at a dosage of $10^4$ to $10^9$ cells/kg body weight, preferably $10^5$ to $10^6$ cells/kg body weight. The cell compositions may also be administered several times at these dosages. The compositions of cells may be injected directly into a tumor, lymph node, or site of infection.

The cells may be activated and expanded to therapeutic effective amounts using methods known in the art.

The cells of the invention may be used in combination with e.g. chemotherapy, radiation, immunomodulatory agents, antibodies or antibody therapies.

Definitions

Unless defined otherwise, technical and scientific terms used herein have the same meaning as commonly understood by one of ordinary skill in the art to which this invention belongs.

In general, a CAR may comprise an extracellular domain (extracellular part) comprising the antigen binding domain, a transmembrane domain and an intracellular signaling domain. The extracellular domain may be linked to the transmembrane domain by a linker. The extracellular domain may also comprise a signal peptide. The extracellular part of the CAR of the present invention also comprises a cytokine receptor activating or blocking domain as disclosed herein.

A "signal peptide" refers to a peptide sequence that directs the transport and localization of the protein within a cell, e.g. to a certain cell organelle (such as the endoplasmic reticulum) and/or the cell surface.

An "antigen binding domain" refers to the region of the CAR that specifically binds to an antigen (and thereby is able to target a cell containing the antigen). The CARs of the invention may comprise one or more antigen binding domains. Generally, the targeting regions on the CAR are extracellular. The antigen binding domain may comprise an antibody or a fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable regions of an immunoglobulin heavy chain and light chain are fused by a flexible linker to form a scFv. Such a linker may be for example the "$(G_4/S_1)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or fragment thereof. Human or humanized antibodies or fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to pass such a spacer. The spacer may include Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

The transmembrane domain of the CAR can be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules are on two (or even more) polypeptides as described above then the CAR may have two (or more) transmembrane domains. The splitting key signaling and antigen recognition modules enables for a small molecule-dependent, titratable and reversible control over CAR cell expression (Wu et al, 2015, Science 350: 293-303) due to small molecule-dependent heterodimerizing domains in each polypeptide of the CAR.

The cytoplasmic domain or the intracellular signaling domain of the CAR is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function. The intracellular signaling domain may include any complete, mutated or truncated part of the intracellular signaling domain of a given protein sufficient to transduce a signal which initiates or blocks immune cell effector functions.

Prominent examples of intracellular signaling domains for use in the CARs include the cytoplasmic signaling sequences of the T cell receptor (TCR) and co-receptors that initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences) and secondly those that act in an antigen-independent manner to provide a secondary or co-stimulatory signal (secondary cytoplasmic signaling sequences, co-stimulatory signaling domain). Therefore, an intracellular signaling domain of a CAR may comprise a primary cytoplasmic signaling domain and/or a secondary cytoplasmic signaling domain.

Primary cytoplasmic signaling sequences that act in a stimulatory manner may contain ITAMs (immunoreceptor tyrosine-based activation motifs signaling motifs).

Examples of ITAM containing primary cytoplasmic signaling sequences often used in CARs are that are those derived from TCR zeta (CD3 zeta), FcR gamma, FcR beta, CD3 gamma, CD3 delta, CD3 epsilon, CD5, CD22, CD79a, CD79b, and CD66d. Most prominent is sequence derived from CD3 zeta.

The cytoplasmic domain of the CAR can be designed to comprise the CD3-zeta signaling domain by itself or combined with any other desired cytoplasmic domain(s). The cytoplasmic domain of the CAR can comprise a CD3 zeta chain portion and a co-stimulatory signaling region. The co-stimulatory signaling region refers to a part of the CAR comprising the intracellular domain of a co-stimulatory molecule. A co-stimulatory molecule is a cell surface molecule other than an antigen receptor or their ligands that is required for an efficient response of lymphocytes to an antigen. Examples for a co-stimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3.

The cytoplasmic signaling sequences within the cytoplasmic signaling part of the CAR may be linked to each other with or without a linker in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3-zeta and the signaling domain of CD28. In another example the cytoplasmic domain may comprise the signaling domain of CD3-zeta and the signaling domain of CD27. In a further example, the cytoplasmic domain may comprise the signaling domain of CD3-zeta, the signaling domain of CD28, and the signaling domain of CD27.

As aforementioned either the extracellular part or the transmembrane domain or the cytoplasmic domain of a CAR may also comprise a heterodimerizing domain for the aim of splitting key signaling and antigen recognition modules of the CAR.

The CAR of the invention (the CAR comprising a cytokine receptor activating or blocking domain) may be designed to comprise any portion or part of the above-mentioned domains as described herein in any combination resulting to a functional CAR. Exemplary the CAR of the invention may have the amino acid sequence of SEQ ID No:3.

The CAR of the invention may be a CAR with at least dual specificity, comprising an extracellular part, at least one intracellular signaling domain, and at least one transmembrane domain, wherein the extracellular part of said CAR comprises a) at least one antigen binding domain, and b) at least one cytokine receptor activating domain or blocking, wherein said at least one antigen binding domain is specific for an antigen of a target cell (first specificity), and wherein said at least one cytokine receptor activating or blocking domain is specific for a cytokine receptor (second specificity) which is not said antigen.

The CAR of the invention which harbors at least one cytokine receptor activating or blocking domain, e.g. at least one cytokine of interest, as a module in the extracellular part of the CAR is a trans-activating CAR. The trans-activating CAR, when expressed on the surface of white blood cells, e.g. T cells direct trans-activity of those cells against target cells expressing the antigen which is recognized by said at least one antigen binding domain of the trans-activating CAR. Trans-activity means the characteristics of the CAR of the invention, that the CAR of the invention comprises at least one domain, i.e. the cytokine receptor activating or blocking domain, that, when expressed on the surface of white blood cells, triggers an activity on the target cell, on the white blood cell expressing said CAR or on another cell, wherein said triggered activity is independent from the binding of the antigen of the target cell by the antigen binding receptor of said CAR. Said triggered activity may be the activation of a cytokine receptor resulting for example in a release of the given cytokine (when said domain is a cytokine receptor activating domain) or may be the blocking of a cytokine receptor resulting for example in a decrease or inhibition of the release of a given cytokine (when said domain is a cytokine receptor blocking domain). The effects of the trans-activity may be further influenced when two or more cytokine receptor activating or blocking domains are used in the CAR of the invention. A CAR with for example two identical cytokine receptor activating or blocking domains may enhance the effects of trans-activity. A CAR with for example two different cytokine receptor activating or blocking domains may diversify the effects of trans-activity as each cytokine receptor activating or blocking domain of such a CAR may trigger different activities on the target cell, on the white blood cell expressing said CAR or on another cell.

Cytokines are a broad and loose category of small proteins (~5-20 kDa) that are important in cell signaling. They are released by cells and affect the behavior of other cells. Cytokines include chemokines, interferons, interleukins, lymphokines, and tumour necrosis factor. Cytokines are produced by a broad range of cells, including immune cells like macrophages, B lymphocytes, T lymphocytes and mast cells, as well as endothelial cells, fibroblasts, and various stromal cells; a given cytokine may be produced by more than one type of cell.

They act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways. They are important in health and disease, specifically in host responses to infection, immune responses, inflammation, trauma, sepsis, cancer, and reproduction.

Each cytokine has a matching cell-surface receptor. Subsequent cascades of intracellular signaling then alter cell functions. This may include the up-regulation and/or down-regulation of several genes and their transcription factors, resulting in the production of other cytokines, an increase in the number of surface receptors for other molecules, or the suppression of their own effect by feedback inhibition The effect of a particular cytokine on a given cell depends on the cytokine, its concentration, the presence of the complementary receptor on the cell surface, and downstream signals activated by receptor binding; these last two factors can vary by cell type.

Interleukin 12 (IL-12) is a cytokine that is naturally produced by dendritic cells, macrophages, neutrophils, and human B-lymphoblastoid cells (NC-37) in response to antigenic stimulation.

It is a heterodimeric cytokine encoded by two separate genes, IL-12A (p35) and IL-12B (p40). The active heterodimer (referred to as 'p70'), and a homodimer of p40 are formed following protein synthesis. IL-12 is involved in the differentiation of naive T cells into Th1 cells. It is known as a T cell-stimulating factor, which can stimulate the growth and function of T cells. It stimulates the production of interferon-gamma (IFN-γ) and tumor necrosis factor-alpha (TNF-α) from T cells and natural killer (NK) cells, and reduces IL-4 mediated suppression of IFN-γ. T cells that produce IL-12 have a co-receptor, CD30, which is associated with IL-12 activity. IL-12 plays an important role in the activities of natural killer cells and T lymphocytes. IL-12 mediates enhancement of the cytotoxic activity of NK cells and CD8+ cytotoxic T lymphocytes.

IL-12 binds to the IL-12 receptor, which is a heterodimeric receptor formed by IL-12R-β1 and IL-12R-β2. IL-12R-β2 is considered to play a key role in IL-12 function, since it is found on activated T cells.

The term "cytokine receptor activating or blocking domain" as used herein refers to an amino acid sequence which is part of the CAR as disclosed herein that is able to bind to and either activates or blocks a cytokine receptor. The cytokine receptor activating domain may be a cytokine agonist. The activation of a particular cytokine receptor by a matching cytokine receptor activating domain of a CAR leads to the activation of the given downstream signals inherent to said cytokine receptor. The amino acid sequence of a cytokine receptor activating domain may comprise the full-length amino acid sequence of a cytokine or may comprise a sequence having a sequence identity of at least 70%, or at least 75%, 80%, 85%, 90%, 95%, 97%, 98% or 99% at the amino acid sequence level to said cytokine. In the context of the present invention, "sequence identity" may be determined using pairwise alignments using alignments programs for amino acid sequences well known to the art.

But the amino acid sequence of a cytokine receptor activating domain can also be a variant of a cytokine which has some amino acids deleted, added, replaced or arranged in another order than the natural cytokine while still retaining the function of the natural full-length cytokine. The amino acid sequence of a cytokine receptor activating domain can also be a functional fragment of a full-length cytokine or a fragment of a full length cytokine having a sequence identity of at least 70%, or at least 75%, 80%, 85%, 90%, 95%, 97%, 98% or 99% at the amino acid sequence level to said cytokine. In this context "functional" means that the fragment is able to bind to and activate the cytokine receptor in a sufficient manner to lead to the activation of the given downstream signals inherent to said cytokine receptor. Preferentially, the cytokine receptor activating domain may be an amino acid sequence of a cytokine or fragment thereof which can bind to and activates a cytokine receptor.

The cytokine receptor blocking domain may be a cytokine antagonist. The blocking or inhibition of a particular cytokine receptor by a matching cytokine receptor blocking domain of a CAR leads to the blocking and/or inhibition of the given downstream signals inherent to said cytokine receptor. The amino acid sequence of a cytokine receptor blocking domain can be a variant of a cytokine which has some amino acids deleted, added, replaced or arranged in another order than the natural cytokine thereby losing the function of said natural cytokine to activate the matching cytokine receptor but saving the function of said natural cytokine to bind to the matching cytokine receptor. The amino acid sequence of a cytokine receptor blocking domain can also be a non-functional fragment of a full-length cytokine or a fragment of a full length cytokine having a sequence identity of at least 70%, or at least 75%, 80%, 85%, 90%, 95%, 97%, 98% or 99% at the amino acid sequence level to said cytokine. In this context "non-functional" means that the fragment is able to bind to and but does not activate the cytokine receptor in a sufficient manner to lead to the activation of the given downstream signals inherent to said cytokine receptor.

The term "antigen" refers to a molecular entity that may be soluble or cell membrane bound in particular but not restricted to molecular entities that can be recognized by means of the adaptive immune system including but not restricted to antibodies or TCRs, or engineered molecules including but not restricted to transgenic TCRs, CARs, scFvs or multimers thereof, Fab-fragments or multimers thereof, antibodies or multimers thereof, single chain antibodies or multimers thereof, or any other molecule that can execute binding to a structure with high affinity. Tumor antigens may be classified into two categories based on their pattern of expression: Tumor-Specific Antigens (TSA), which are present only on tumor cells and not on any other cell and Tumor-Associated Antigens (TAA), which are present on some tumor cells and also some normal cells.

The term "target cells" as used herein refers to cells which express the antigen on their cell surface which should be recognized (bound) by an antigen binding domain of the CAR. Carcinoembryonic antigen (CEA; CD66e) describes a set of highly related glycoproteins involved in cell adhesion. CEA is produced in gastrointestinal tissue during fetal development, and is present on the luminal site of gastrointestinal and lung epithelia of adults. Soluble CEA is found in the sera of healthy individuals and increases during inflammation and malignant diseases, in particular in patients with adenocarcinoma of the gastrointestinal tract, mammary, ovary and others.

The CARs (polypeptide(s)), the nucleic acid molecule(s) encoding the CARs, recombinant expression vectors, cells expressing the CARs, and populations of cells expressing the CARs, and can be isolated and/or purified. For example, a purified (or isolated) cell preparation is one in which the cell population is purer than the cell population in their natural environment within the body. Such cells may be produced, for example, by standard purification techniques, e.g. cell magnetic separation methods such as MACS® (Miltenyi Biotec GmbH, Germany) or flow cytometric separation methods such as FACS® (Beckton Dickinson).

In some embodiments, a preparation of a cell is purified such that the cell represents at least about 50%, for example at least about 70%, of the total cell content of the preparation. For example, the purity can be at least about 50%, can be greater than about 60%, about 70% or about 80%, or can be about 100%.

The term "tumor" is known medically as a neoplasm. Not all tumors are cancerous; benign tumors do not invade neighboring tissues and do not spread throughout the body.

The term "cancer" is known medically as a malignant neoplasm. Cancer is a broad group of diseases involving unregulated cell growth and includes all kinds of leukemia. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

The terms "Chemotherapy" or "chemotherapeutic treatment" refer to the treatment of cancer (cancerous cells) with one or more cytotoxic anti-neoplastic drugs ("chemotherapeutic agents" or "chemotherapeutic drugs") as part of a standardized regimen. Chemotherapy may be given with a curative intent or it may aim to prolong life or to palliate symptoms. It is often used in conjunction with other cancer treatments, such as radiation therapy, surgery, and/or hyperthermia therapy. Traditional chemotherapeutic agents act by killing cells that divide rapidly, one of the main properties of most cancer cells. This means that chemotherapy also harms cells that divide rapidly under normal circumstances: cells in the bone marrow, digestive tract, and hair follicles. This results in the most common side-effects of chemotherapy: myelosuppression (decreased production of blood cells, hence also immunosuppression), mucositis (inflammation of the lining of the digestive tract), and alopecia (hair loss).

Some newer anticancer drugs (for example, various monoclonal antibodies or engineered cells like those of the present invention) are not indiscriminately cytotoxic, but rather target proteins that are abnormally expressed in cancer cells and that are essential for their growth. Such treatments are often referred to as "targeted therapy" (as distinct from classic chemotherapy) and are often used alongside traditional chemotherapeutic agents in antineoplastic treatment regimens. Immunotherapy is a medical term defined as the "treatment of disease by inducing, enhancing, or suppressing an immune response" Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based, preferentially T cell-based cytotoxic responses to attack cancer cells (cellular therapy). T cells that have a natural or genetically engineered reactivity to a patient's cancer are generated in vitro and then transferred back into the cancer patient.

The term "treatment" as used herein means to reduce the frequency or severity of at least one sign or symptom of a disease.

The term "biomarker" or "marker" is widespread in the art and may broadly denote a biological molecule and/or a detectable portion thereof (e.g. a nucleic acid, a peptide or a lipid such as a glycolipid) whose qualitative and/or quantitative evaluation in an subject is predictive or informative (e.g., predictive, diagnostic and/or prognostic) with respect to one or more aspects of the individual's phenotype and/or genotype, such as, for example, with respect to the status of the individual.

As used herein, the term "subject" refers to an animal. Preferentially, the subject is a mammal such as mouse, rat, cow, pig, goat, chicken dog, monkey or human. More preferentially, the subject is a human. The subject may be a subject suffering from a disease such as cancer (a patient), but the subject may be also a healthy subject.

The term "autologous" as used herein refers to any material derived from the same subject to who it is later re-introduced.

The term "allogeneic" as used herein refers to any material derived from a different subject of the same species as the subject to who the material is re-introduced.

The term "therapeutically effective amount" means an amount which provides a therapeutic benefit in a subject.

The terms "specifically binds" or "specific for" with respect to an antigen-binding domain of an antibody, of a fragment thereof or of a CAR refer to an antigen-binding domain which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain that specifically binds to an antigen may bind also to different allelic forms of the antigen (allelic variants, splice variants, isoforms etc.). This cross reactivity is not contrary to the definition of that antigen-binding domain as specific.

The terms "engineered cell" and "genetically modified cell" as used herein can be used interchangeably. The terms mean containing and/or expressing a foreign gene or nucleic acid sequence which in turn modifies the genotype or phenotype of the cell or its progeny. Especially, the terms refer to the fact that cells, preferentially T cells can be manipulated by recombinant methods well known in the art to express stably or transiently peptides or proteins which are not expressed in these cells in the natural state. For example T cells are engineered to express an artificial construct such as a chimeric antigen receptor on their cell surface. For example, the CAR sequences may be delivered into cells using a retroviral or lentiviral vector.

The term "immune cell" or "immune effector cell" refers to a cell that may be part of the immune system and executes a particular effector function such as alpha-beta T cells, NK cells, NKT cells, B cells, innate lymphoid cells (ILC), cytokine induced killer (CIK) cells, lymphokine activated killer (LAK) cells, gamma-delta T cells, mesenchymal stem cells or mesenchymal stromal cells (MSC), monocytes or macrophages. Preferred immune cells are cells with cytotoxic effector function such as alpha-beta T cells, NK cells, NKT cells, ILC, CIK cells, LAK cells or gamma-delta T cells. "Effector function" means a specialized function of a cell, e.g. in a T cell an effector function may be cytolytic activity or helper activity including the secretion of cytokines.

The term "closed system" as used herein refers to any closed system which reduces the risk of cell culture contamination while performing culturing processes such as the introduction of new material and performing cell culturing steps such as proliferation, differentiation, activation, genetic modification and/or separation of cells. Such a system allows to operate under GMP or GMP-like conditions ("sterile") resulting in cell compositions which are clinically applicable.

An example for a closed system is the CliniMACS Prodigy® (Miltenyi Biotec GmbH, Germany, WO2009/072003).

The terms "automated method" or "automated process" as used herein refer to any process being automated through the use of devices and/or computers and computer software which otherwise would or could be performed manually by an operator. Methods (processes) that have been automated require less human intervention and less human time to deliver. In some instances a method is automated if at least one step of the method is performed without any human support or intervention. Preferentially the method is automated if all steps of the method are performed without human support or intervention.

This invention is further illustrated by the following examples, which are not to be construed in any way as imposing limitations upon the scope thereof.

EXAMPLES

Example 1: Expression of the CAR with IL-12 Receptor Activating Domain (Hereafter: IL12-CAR) in T Cell Subsets Engraftment of Peripheral Blood T Cells with IL12-CAR.

Figure 1:
FIG. 1: Modular composition of the IL12-CAR.
(A) Expression cassette of conventional $2^{nd}$ generation anti-CEA CAR.
(B) Expression cassette of the hybrid CAR with the CEA antigen binding domain and the IL-12 receptor activating domain (anti-CEA-IL12-CAR).
Figure 1:
Figure 2:
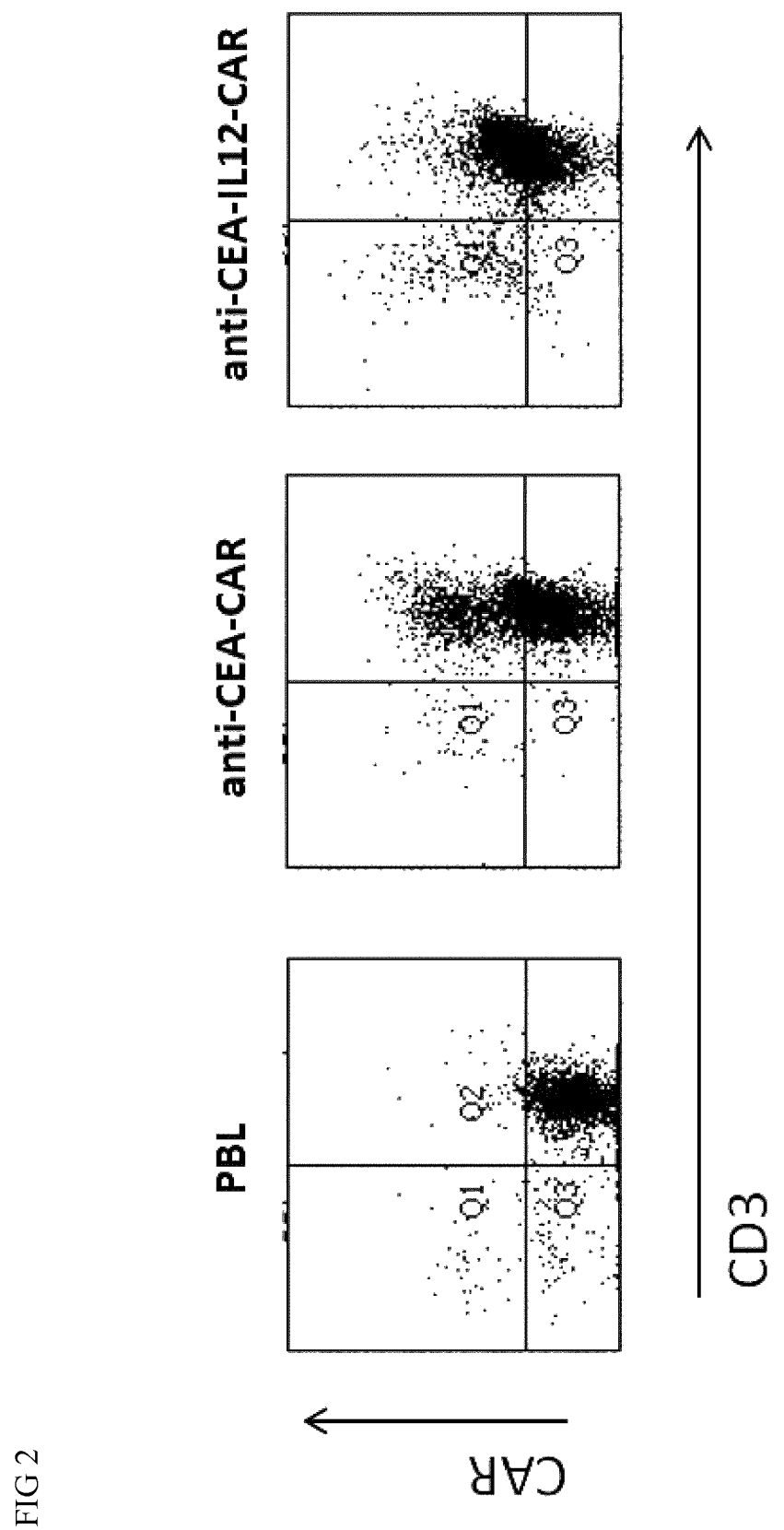
FIG. 2: Expression of CARs by peripheral blood T cells.
T cells of peripheral blood were transduced to express a conventional 2nd generation anti-CEA CAR or the hybrid anti-CEA-IL12-CAR, respectively. CARs were detected on the cell surface by two-color flow cytometry utilizing an anti-human IgG and anti-CD3 antibody, respectively.

T cells were Ficoll isolated from peripheral blood, activated in presence of agonistic anti-CD3 and anti-CD28 antibodies (100 ng/ml each) and 500 U/ml IL2, respectively. Activated T cells were retrovirally transduced with a vector encoding the IL12-CAR or a CAR without IL12 receptor activating domain (FIG. 1). The antibody-derived antigen binding domain of both CARs is directed against the CEA tumor antigen. Transduced T cells were stained with anti-CD3 mAb and an anti-human IgG antibody to monitor CAR expression (FIG. 2). The IL12-CAR was expressed in peripheral T cells with similar efficiency than the CAR without IL12 receptor activating domain.

IL12-CAR is Expressed in Different T Cell Subsets.

Figure 3:
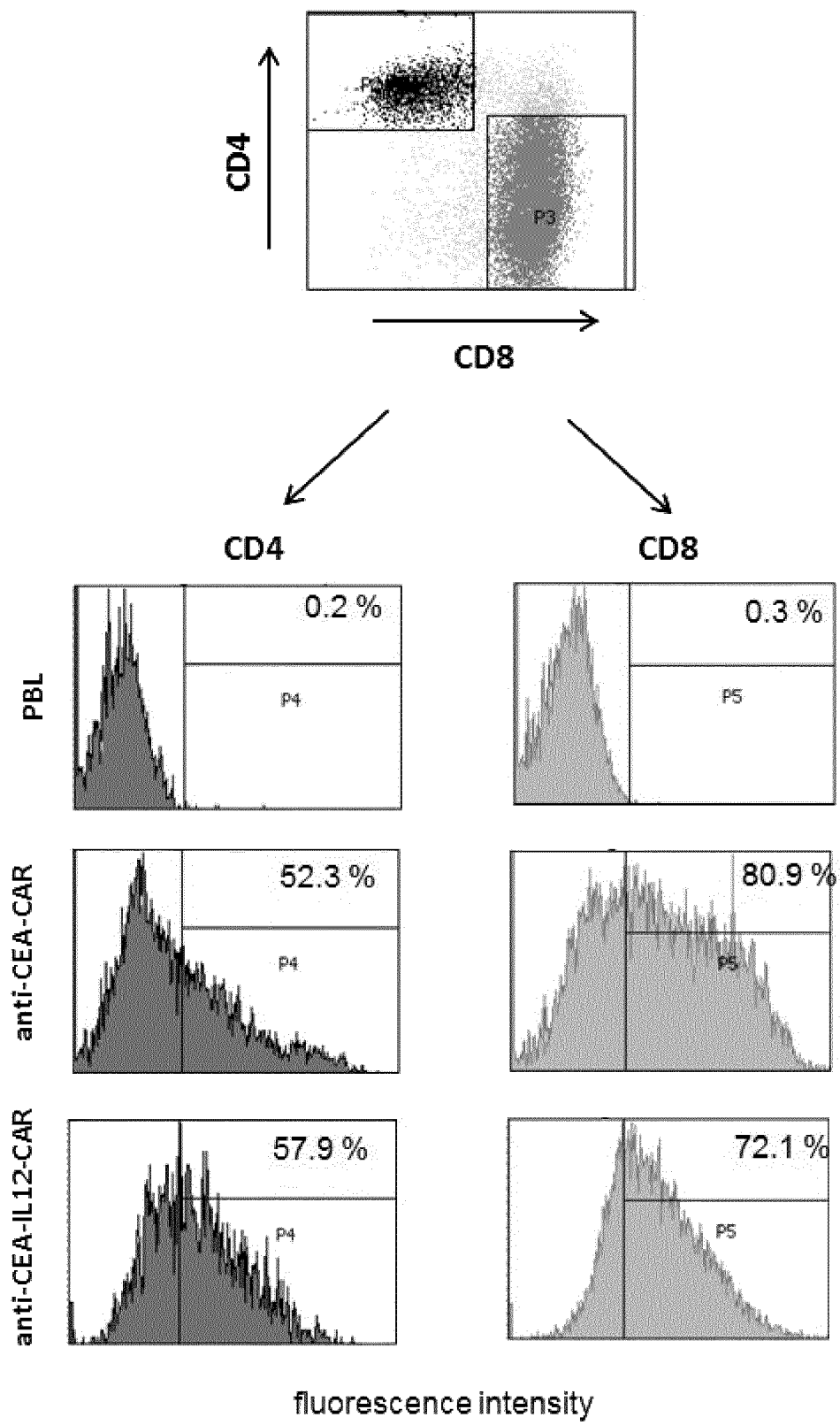
FIG. 3: Anti-CEA-IL12-CAR is expressed in different T cell subsets.
T cells of peripheral blood were transduced to express a conventional 2nd generation anti-CEA-CAR or the hybrid anti-CEA-IL12-CAR, respectively. CAR expression in CD4+ and CD8+ T cells was recorded by three-color flow cytometry utilizing anti-human IgG and anti-CD4 and anti-CD8 antibodies, respectively. CD4+ and CD8+ T cells were gated and the number of CAR+ cells on T cell subsets was determined.

Peripheral T cells were transduced with the IL12-CAR as described above. CAR expression in CD4 and CD8 T cells was monitored utilizing anti-CD4 and anti-CD8 antibodies, respectively, and an anti-human IgG Fc antibody for monitoring CAR expression (FIG. 3). We detected high numbers of CD4 and CD8 T cells with expression of the IL12-CAR. In contrast to the CAR without IL12 receptor activating domain, that was more efficiently expressed in CD8+ T cells, the IL12-CAR was expressed in CD4+ and CD8+ T cell subsets with similar efficiency.

Conclusion:

The IL12-CAR is efficiently expressed in primary peripheral T cells. Thereby the IL12-CAR is expressed in CD4 and CD8 T cells with similar efficiency making both T cell subsets for redirecting by the IL12-CAR.

Example 2: IL12-CAR Induces a CD56+CD62L+ Phenotype of Engineered T Cells

Figure 4:
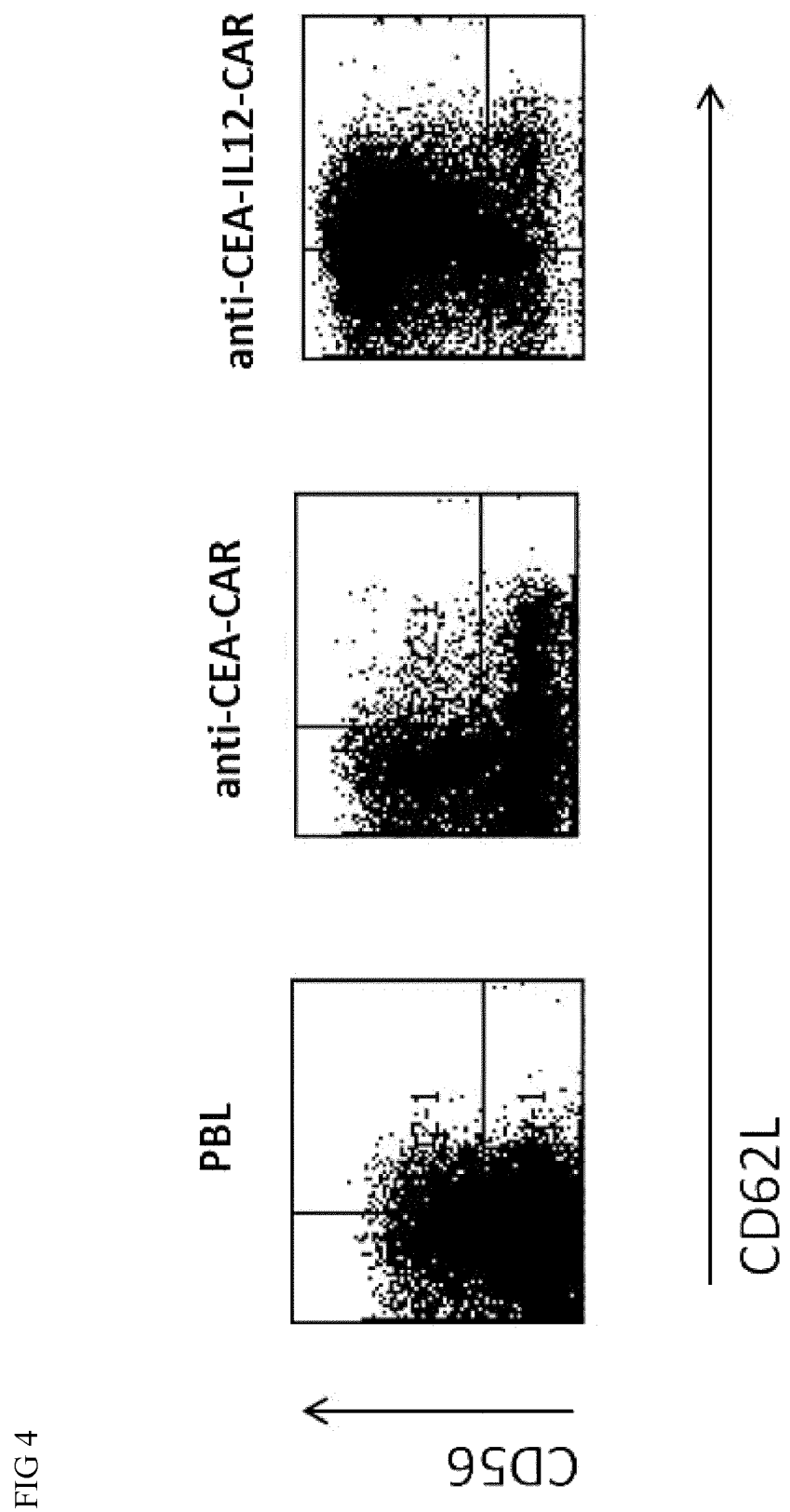
FIG. 4: Anti-CEA-IL12-CAR induces CD56+CD62L+ T cells.
Anti-CEA-CAR T cells, anti-CEA-IL12-CAR T cells and non-transduced T cells, respectively, were cultivated for 9 d after transduction in presence of IL2 (500 U/ml) and analyzed for CD56 and CD62L expression by multi-color flow cytometry. Data represent dot blots of a typical experiment.

T cells were isolated from peripheral blood, activated in the presence of agonistic anti-CD3 and anti-CD28 mAbs (100 ng/ml each) and 500 U/ml IL, respectively. Activated T cells were retrovirally transduced with a vector encoding the IL12-CAR or CAR without cytokine receptor activating domain for control according to standard operation protocol. Transduced T cells were cultivated for 9 d and stained with anti-CD3, anti-CD56, and anti-CD62L antibodies (FIG. 4). The IL12-CAR induced preferentially a CD56+CD62L+ phenotype of IL12-CAR T cells.

Conclusion:

The phenotype of IL12-CAR transduced T cells resemble the phenotype of IL12 maturated NK/NKT cells that were reported to acquire an improved therapeutic potential (Lehman D et al., PLoS One 9, e87131, 2014)

Example 3: IL12-CAR Signaling Results in Improved IFN-Gamma Secretion

IFN-gamma secretion is substantial for an efficient antitumor response of adoptively transferred CAR T cells.

Figure 5:
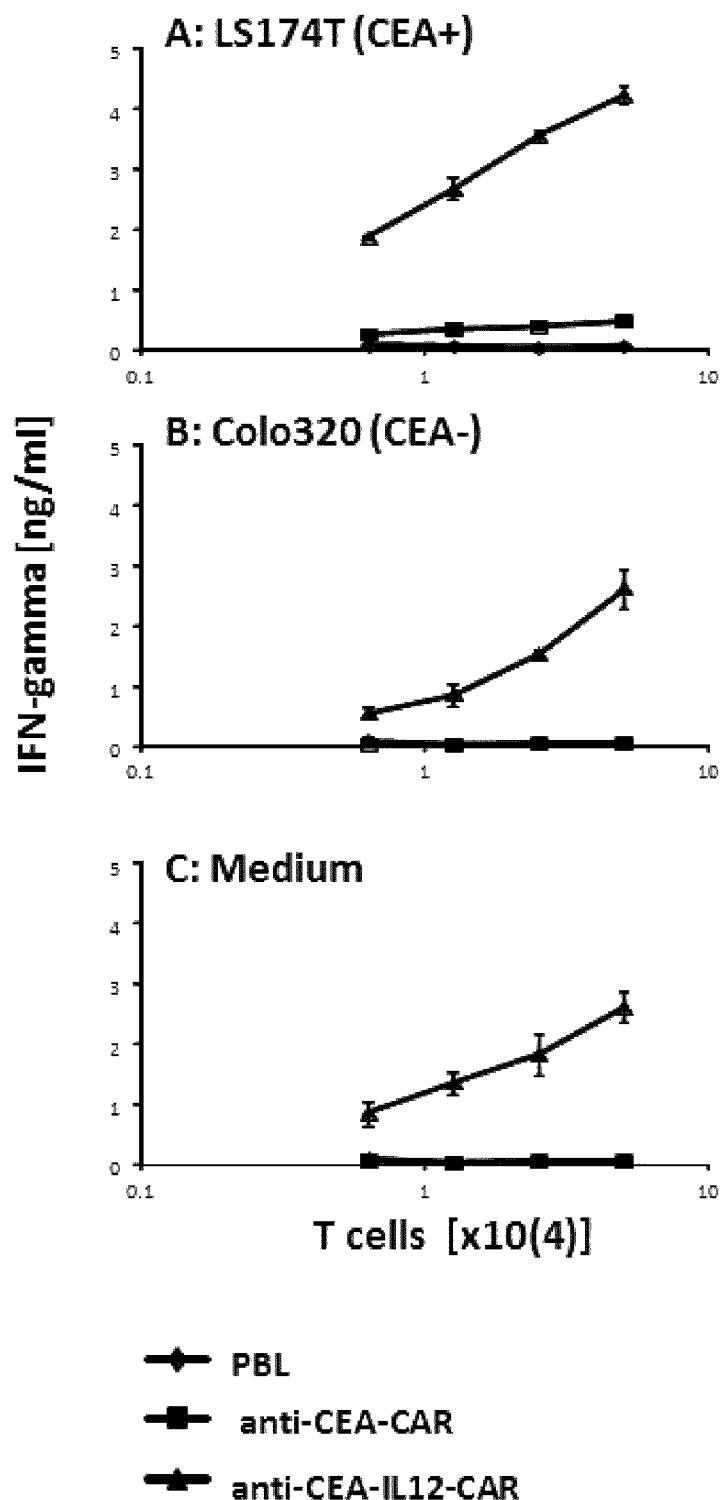
FIG. 5: Enhanced IFN-gamma secretion by combined cis and trans signaling of the hybrid anti-CEA-IL12-CAR.
CAR T cells (0.313-2.5×10(4)/well) were co-cultivated for 48 h with CEA+ LS174T, CEA-Colo320 tumor cells (each 2.5×10(4)/well) and without target cells, respectively. After 48 h, supernatants were removed and tested for IFN-gamma secretion by ELISA. Data represent mean of triplicates+−standard deviation (SD).

Accordingly, a CAR with high IFN-gamma inducing capability will be valuable for clinical application. To test IFN-gamma secretion properties of IL12-CAR, T cells from the peripheral blood were isolated and transduced to express the IL12-CAR and for comparison a CAR without cytokine receptor binding domain as described above. CAR T cells were co-cultivated with CEA+ LS174T and CEA− Colo320 tumor cells, respectively, for 48 h and IFN-gamma secretion was recorded by ELISA. T cells expressing the IL12-CAR secreted substantial more IFN-gamma upon antigen encounter than T cells with the CAR without IL12-receptor activating domain (FIG. 5). Moreover, even in the absence of antigen IL12-CAR T cells secreted IFN-gamma that will modulate the tumor environment to become more susceptible for a cellular immune attack.

Conclusion:

The IL12-CAR has improved cytokine secretion properties due to synergistic signaling via the CAR-signaling domain and the IL12 receptor activating domain. The improved secretion of pro-inflammatory cytokines will be suitable to reprogram the tumor microenvironment to recruit additional adoptive and innate anti-tumor reactivity.

Example 4: IL12-CAR Improves Tumor Cell Killing

Figure 7:
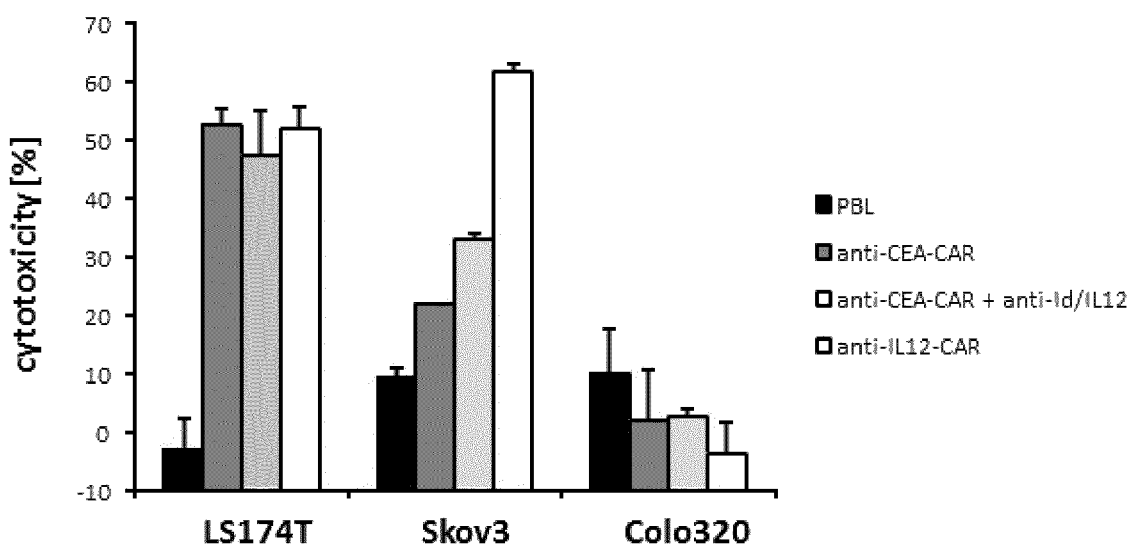
FIG. 7: Hybrid anti-CEA-IL12-CAR is superior to conventional anti-CEA-CAR with combined stimulation by CAR and exogenous IL12.
Conventional CAR T cells were cultivated in presence of IL2 (500 U/ml) or conditioned for 72 h in presence of the CAR-specific anti-idiotypic antibody BW2064 (4 µg/ml) and exogenous mIL12 (5 ng/nml) and IL2 (500 U/ml).

T cells from the peripheral blood were engineered to express the IL12-CAR or for comparison with wild type CAR without cytokine receptor activating domain. CAR T cells were co-cultivated (0.625×10(4)-5×10(4)/well) with CEA+ LS174T and hard to kill Skov3 tumor cells, respectively, or CEA− Colo320 tumor cells (each 2.5×10(4)/well) for 48 h. Tumor cell viability was recorded by a tetrazolium-salt based XTT-assay and percent cytotoxicity was calculated as follows: cytotoxicity [%]=100−viability [%]. Whereas T cells with wild type CAR and IL12-CAR, respectively, lysed CEA+ LS174T tumor cells with similar efficiency, IL12-CAR T cells killed Skov3 tumor cells with much higher efficiency than CAR T cells without IL12 receptor activating domain (FIG. 6). In contrast, CEA− tumor cells were not killed by CAR T cells indicating antigen-specificity of the CAR. Improved killing of Skov3 tumor cells was partly due to simultaneous signaling via the CAR and the IL12 receptor activating domain because stimulation of the wild type CAR with an anti-idiotypic antibody against the CAR binding domain and exogenous IL12 improved killing of Skov3 cells by CAR T cells without IL12 receptor activating domain. Surprisingly, the IL12-CAR was still more effective and additional stimulation via exogenous IL12 and the anti-idiotypic antibody did not further enhance killing of Skov3 cells (FIG. 7).

Conclusion:

The IL12-CAR improved target cell killing especially of tumor cells that were less susceptible for a T cells attack like Skov3 ovarian tumor cells. On the other hand improved killing properties of IL12-CAR T cells did not result in overall non-specific killing of target cells as demonstrated by co-cultivation with CEA− Colo320 tumor cells. Since improved cytolytic anti-tumor activity was not induced by simultaneous application of an agonistic ligand for the antigen binding domain of the CAR and the IL12 receptor, respectively, we conclude that improved targeting of Skov tumor cells is due to intrinsic properties of the modified IL12-CAR T cell itself and not solely to the combination of different T cell activating agents.

Example 5: IL12 CAR Mediated T Cell Activation is Superior to CAR T Cell Activation and Simultaneous IL2 and IL12 Stimulation IL2 and IL12 enhance synergistically the function of T cells against tumor cells. We tested simultaneous application of exogenous IL2 and IL12 on target cell lysis of IL12-CAR and CAR T cells, respectively, against Skov3 tumor cells. We found no impact of exogenous IL2 and IL12 on CAR mediated lysis of Skov3 cells. Moreover, IL12-CART cells demonstrated superior lysis of Skov3 cells compared to CAR T cells irrespective of the presence or absence of exogenous IL2 or IL12 or both IL2 and IL12, respectively (FIG. 8).

Conclusion:

IL12-CAR induces superior cytolysis of Skov3 tumor cells that is not modulated by exogenous pro-inflammatory cytokines like IL2 and IL12 or the combination of both. Improved target cell lysis appears moreover to be due to intrinsic properties of the IL12-CAR.

Example 6: IL12 CAR T Cells Inhibit In Vivo Growth of Established Skov3 Tumors in Immune Deficient Rag−/− Common Gamma−/− Mice T cells were engineered to express IL12-CAR and CAR without IL12 receptor activating domain according to SOP and CAR expression was monitored by FACS. Rag−/− common gamma−/− mice were engrafted with 5×10(6) Skov3 tumor cells/mouse. After 7 days one dose of 1×10(7) total T cells per mouse was injected into tail veins of mice with established tumors. The number of CAR T cells was 14% (anti-CEA-CAR) and 9% (anti-CEA-IL12-CAR), respectively. Tumor growth was recorded every $2^{nd}$-$3^{rd}$ day and tumor volume was determined (FIG. 9). Whereas the CAR-modified T cells and T cells without CAR were not effective in suppressing tumor growth, IL12-CAR T cells substantially inhibited growth of Skov3 tumors.

Conclusion:

IL12-CAR T cells suppressed tumor growth of Skov3 cells indicating sustained anti-tumor reactivity in vivo.

Example 7: An IL-12 CAR with Specificity for Muc1

An IL-12 CAR was engineered which harbors the anti-Muc1 scFv as a CAR targeting domain instead of the anti-CEA targeting domain (FIG. 10). The CAR is of the same modular composition as the anti-CEA CAR, however, with a different targeting specificity (cf. FIG. 1). For comparison, an anti-Muc1 CAR was engineered without integrated IL-12.

T cells from the peripheral blood were retrovirally transduced to express the anti-CEA-IL12-CAR or the anti-Muc1-IL12-CAR, respectively. CARs were detected on the surface of T cells by flow cytometry utilizing an anti-human IgG antibody, which detects the common extracellular spacer domain, and anti-CD3 antibody, respectively, to verify the T cells (FIG. 11).

Conclusion:

T cells express the anti-CEA-IL12 CAR and the anti-Muc1-IL12 CAR, respectively, on the cell surface after retroviral transduction.

Example 8: The Anti-Muc1 IL12-CAR Improved T Cell Activation Upon Antigen Engagement The anti-Muc1-IL12-CAR T cells were co-cultivated for 48 h with Muc1+ LS174T and Muc1− Colo320 tumor cells, respectively. After 48 h, more IFN-γ was recorded by ELISA in the supernatants of IL12-CAR T cells than of CART cells without IL12 upon engagement of Muc1+ tumor cells (FIG. 12). There is some IFN-γ release of IL12-CAR T cells in the presence of Muc1− tumor cells indicating the induction of antigen independent IFN-γ secretion by IL12-CAR T cells which is not the case for CAR T cells.

To assay the cytolytic activity, anti-Muc1-IL12-CAR T cells and anti-Muc1-CAR T cells, respectively, were co-incubated in increasing cell numbers with Muc1+ MCF7 mammary carcinoma cells in vitro and the tumor cell survival was recorded. As summarized in FIG. 13, MCF7 cells were more efficiently lysed by anti-Muc1-IL12-CAR T cells at low T cell numbers than by anti-Muc1-CAR T cells. The CAR specifically mediated killing of MCF7 cells since T cells without CAR did not produce dose-dependent cytolysis.

Conclusion:

The IL12-CAR showed an improved antigen dependent T cell activation indicated by increased IFN-γ release and cytolytic activity compared with CAR T cells of the same specificity but without IL12. In the absence of antigen, IL12-CAR T cells released IFN-γ which, however, was lower than in the presence of the CAR cognate antigen.

Example 9: Specific Tumor Cell Lysis by IL12-CAR T Cells

Anti-Muc1-IL12-CAR, anti-CEA-IL12 CAR T cells and non-modified T cells for control, respectively, were co-cultivated with CEA+Muc1+ LS174T and MCF7 or CEA−Muc1− Colo 320 tumor cells. The cytolytic activity was determined after 48 hrs (FIG. 13). T cells with anti-CEA-IL12 CAR eliminated CEA+ LS174T and MCF-7 cells but not CEA− Colo320 cells. Accordingly, T cells with the anti-Muc1-IL12 CAR eliminated Muc1+ LS174T and MCF-7 cells but not Muc1− Colo320 cells. For comparison non-modified T cells did not exhibit substantial cytolytic activity towards the target cells.

Conclusion:

The anti-CEA and anti-Muc CAR with integrated IL12 domain mediated antigen-specific and dose-dependent killing of target cells.

Example 10: Anti-CEA-IL12 CAR T Cells do not Lyse CEA− Normal Fibroblasts

We addressed whether the IL12-CAR induced change towards a NKT cell phenotype of engineered T cells (cf. FIG. 4) goes along with an antigen-independent lysis of healthy cells. T cells with anti-CEA-CAR, anti-CEA-IL12-CAR and non-transduced T cells were co-cultivated with CEA− normal fibroblasts and for comparison with CEA+ LS 174T and CEA− Colo320 tumor cells. After 48 hrs cell viability was recorded (FIG. 14). Data demonstrate preferential lysis of CEA+ tumor cells by T cells with the anti-CEA-IL12-CAR whereas CEA− fibroblasts and CEA− tumor cells were not substantially affected.

Conclusion:

T cells with anti-CEA-IL12-CAR did not eliminate normal healthy fibroblasts in vitro.

Example 11: A CAR with IL7 in the Terminal Position

We engineered a second prototype of cytokine CAR with two modifications; the harbors IL7 instead of IL12 and has the cytokine in the terminal position of the molecule (FIG. 15). The CAR has a targeting specificity for CEA provided by the BW431/26 scFv. IL7 and the anti-CEA scFv are linked by a Gly-Ser linker.

Upon retroviral transduction the IL7-CAR with specificity for CEA was expressed by human peripheral blood T cells as revealed by flow cytometry (FIG. 16). The anti-CEA CAR without IL7 was expressed by T cells for comparison.

Conclusion:

A cytokine CAR with IL7 and the cytokine in a terminal position were efficiently expressed by modified T cells.

Example 12: Preferential Amplification of CD8+ T Cells with IL7-Anti-CEA CAR We addressed whether T cells with the IL7-anti-CEA CAR have an advantage with respect to survival and/or amplification. T cells were engineered with the IL7-anti-CEA CAR and for comparison with the anti-CEA CAR without IL7. After 48 h in the presence of IL2 the frequency of CAR T cells was the same, however, after 144 h the frequency of T cells with the IL7-anti-CEA CAR were higher than of T cells with the anti-CEA CAR without IL7 (FIG. 17A). Both CD4+ and CD8+ T cells with IL7-anti-CEA CAR amplified in vitro with higher efficiency than T cells with the anti-CEA CAR. Moreover, CD8+ CAR T cells increased to higher frequencies than CD4+ T cells (FIG. 17B).

Conclusion:

Data demonstrate a preferential expansion of T cells with IL7 CAR compared with CAR T cells without IL7. CD8+ T cells in particular did benefit from the IL7 CAR with respect to amplification and/or survival.

Example 13: Improved Cytolytic Activity of T Cells with IL7-Anti-CEA CAR

Human T cells from the peripheral blood were engineered with the IL7-anti-CEA CAR and with the anti-CEA CAR without IL7, respectively. Un-modified T cells served as control. T cells were co-incubated with CEA+ LS174T cells and CEA− Colo320 cells and viability of tumor cells determined after 48 hrs.

Conclusion:

Data demonstrate antigen-specific and efficient lysis of antigen-positive tumor cells by IL7-anti-CEA-CAR T cells; antigen-negative cells were not lysed.

The invention claimed is:

1. A single chain chimeric antigen receptor (CAR) polypeptide, comprising an extracellular part, wherein the extracellular part of the CAR comprises: a) a scFv and b) the amino acid sequence encoded by SEQ ID NO: 1.

2. The single chain CAR polypeptide according to claim 1, wherein the scFv binds to carcinoembryonic antigen (CEA).

3. The single chain CAR polypeptide according to claim 1, wherein the scFv binds to Mucin-1 (Muc1).

4. The single chain CAR polypeptide according to claim 1, wherein the CAR comprises the amino acid sequence encoded by SEQ ID NO:4 or SEQ ID NO:5.

5. An isolated nucleic acid molecule encoding the CAR according to claim 4.

6. A T cell comprising the nucleic acid molecule of claim 5.

7. A pharmaceutical composition comprising the cell according to claim 6.

8. A T cell expressing the CAR according to claim 4.

9. A method for treating a cancer in a subject in need thereof, the method comprising administering to the subject an anti-tumor effective amount of the cell according to claim 8, wherein the cancer comprises leukemia, lymphoma, multiple myeloma, adenocarcinoma or carcinoma of the gastrointestinal tract, mammary gland, ovary, prostate, liver lung, kidney, or a combination thereof.

10. The T cell according to claim 8, wherein said CAR is constitutively expressed.

11. A T cell comprising a chimeric antigen receptor comprising an extracellular domain comprising an scFv and the amino acid sequence encoded by SEQ ID NO: 1.

* * * * *

SEQUENCE LISTING

```
<160> NUMBER OF SEQ ID NOS: 15

<210> SEQ ID NO 1
<211> LENGTH: 1617
<212> TYPE: DNA
<213> ORGANISM: artificial sequence
```

```
<220> FEATURE:
<223> OTHER INFORMATION: Mouse-derived  p40-p35 IL12

<400> SEQUENCE: 1
gatcccgccg agcccaaatc tcctgacaaa actcatacat gcccaccaat gtgggagctg      60
gagaaagacg tttatgttgt agaggtggac tggactcccg atgcccctgg agaaacagtg     120
aacctcacct gtgacacgcc tgaagaagat gacatcacct ggaccTcaga ccagagacat     180
ggagtcatag gctctggaaa gaccctgacc atcactgtca aagagtttct agatgctggc     240
cagtacacct gccacaaagg aggcgagact ctgagccact cacatctgct gctccacaag     300
aaggaaaatg gaatttggtc cactgaaatt ttaaaaaatt tcaaaaacaa gactttcctg     360
aagtgtgaag caccaaatta ctccggacgg ttcacgtgct catggctggt gcaaagaaac     420
atggacttga agttcaacat caagagcagt agcagtcccc ccgactctcg ggcagtgaca     480
tgtggaatgg cgtctctgtc tgcagagaag gtcacactgg accaaaggga ctatgagaag     540
tattcagtgt cctgccagga ggatgtcacc tgcccaactg ccgaggagac cctgcccatt     600
gaactggcgt tggaagcacg gcagcagaat aaatatgaga actacagcac cagcttcttc     660
atcagggaca tcatcaaacc agaccgcc aagaacttgc agatgaagcc tttgaagaac       720
tcacaggtgg aggtcagctg ggagtaccct gactcctgga gcactcccca ttcctacttc     780
tccctcaagt tctttgttcg aatccagcgc aagaaagaaa agatgaagga cagagggag      840 gggtgtaacc agaaaggtgc gttcctcgta gagaagacat ctaccgaagt ccaatgcaaa     900
ggcgggaatg tctgcgtgca agctcaggat cgctattaca attcctcatg cagcaagtgg     960
gcatgtgttc cctgcagggt ccgatccggt ggcggtggct cgggcggtgg tgggtcgggt    1020
ggcggcggat ctagggtcat tccagtctct ggacctgcca ggtgtcttag ccagtcccga    1080
aacctgctga gaccacaga tgacatggtg aagacggcca gagaaaagct gaaacattat      1140
tcctgcactg ctgaagacat cgatcatgaa gacatcacac gggaccaaac cagcacattg    1200
aagacctgtt taccactgga actacacaag aacgagagtt gcctggctac tagagagact    1260
tcttccacaa caagagggag ctgcctgccc ccacagaaga cgtctttgat gatgaccctg    1320
tgccttggta gcatctatga ggacttgaag atgtaccaga cagagttcca ggccatcaac    1380
gcagcacttc agaatcacaa ccatcagcag atcattctag acaagggcat gctggtggcc    1440
atcgatgagc tgatgcagtc tctgaatcat aatggcgaga ctctgcgcca gaaacctcct    1500
gtgggagaag cagacccta cagagtgaaa atgaagctct gcatcctgct tcacgccttc    1560
agcacccgcg tcgtgaccat caacagggtg atgggctatc tgagctccgc cggagat      1617

<210> SEQ ID NO 2
<211> LENGTH: 555
<212> TYPE: DNA
<213> ORGANISM: artificial sequence
<220> FEATURE:
<223> OTHER INFORMATION: Hybrid CD28dlckzeta signaling chain (human)

<400> SEQUENCE: 2
gatcccaaat tttgggtgct ggtggtggtt ggtggagtcc tggcttgcta tagcttgcta      60
gtaacagtgg cctttattat tttctgggtg aggagtaaga ggagcaggct cctgcacagt     120
gactacatga acatgactcc ccgccgcccc gggcccaccc gcaagcatta ccaggcctat     180
gccgccgcac gcgacttcgc agcctatcgc tccctgagag tgaagttcag caggagcgca     240
gacgcccccg cgtaccagca gggccagaac cagctctata acgagctcaa tctaggacga    300
```

```
agagaggagt acgatgtttt ggacaagaga cgtggccggg accctgagat gggggggaaag    360 ccgagaagga agaaccctca ggaaggcctg tacaatgaac tgcagaaaga taagatggcg    420
gaggcctaca gtgagattgg gatgaaaggc gagcgccgga ggggcaaggg gcacgatggc    480
ctttaccagg gtctcagtac agccaccaag gacacctacg acgcccttca catgcaggcc    540
ctgccccctc gctaa                                                     555
```

<210> SEQ ID NO 3
<211> LENGTH: 1224
<212> TYPE: PRT
<213> ORGANISM: artificial sequence
<220> FEATURE:
<223> OTHER INFORMATION: anti-CEA-IL12-CAR (mouse/human)

<400> SEQUENCE: 3

```
Met Asp Phe Gln Val Gln Ile Phe Ser Phe Leu Leu Ile Ser Ala Ser
1               5                   10                  15

Val Ile Met Ser Arg Gly Val His Ser Gln Val Gln Leu Gln Glu Ser
            20                  25                  30

Gly Pro Gly Leu Val Arg Pro Ser Gln Thr Leu Ser Leu Thr Cys Thr
        35                  40                  45

Val Ser Gly Phe Thr Ile Ser Ser Gly Tyr Ser Trp His Trp Val Arg
    50                  55                  60

Gln Pro Pro Gly Arg Gly Leu Glu Trp Ile Gly Tyr Ile Gln Tyr Ser
65                  70                  75                  80

Gly Ile Thr Asn Tyr Asn Pro Ser Leu Lys Ser Arg Val Thr Met Leu
                85                  90                  95

Val Asp Thr Ser Lys Asn Gln Phe Ser Leu Arg Leu Ser Ser Val Thr
            100                 105                 110

Ala Ala Asp Thr Ala Val Tyr Tyr Cys Ala Arg Glu Asp Tyr Asp Tyr
        115                 120                 125

His Trp Tyr Phe Asp Val Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Thr Ile Thr Cys Ser Thr Ser Ser Val Ser Tyr Met
            180                 185                 190

His Trp Tyr Gln Gln Lys Pro Gly Lys Ala Pro Lys Leu Leu Ile Tyr
        195                 200                 205

Ser Thr Ser Asn Leu Ala Ser Gly Val Pro Ser Arg Phe Ser Gly Ser
    210                 215                 220

Gly Ser Gly Thr Asp Phe Thr Phe Thr Ile Ser Ser Leu Gln Pro Glu
225                 230                 235                 240

Asp Ile Ala Thr Tyr Tyr Cys His Gln Trp Ser Ser Tyr Pro Thr Phe
                245                 250                 255

Gly Gln Gly Thr Lys Val Glu Ile Lys Val Asp Pro Ala Glu Pro Lys
            260                 265                 270

Ser Pro Asp Lys Thr His Thr Cys Pro Pro Met Trp Glu Leu Glu Lys
        275                 280                 285

Asp Val Tyr Val Val Glu Val Asp Trp Thr Pro Asp Ala Pro Gly Glu
    290                 295                 300

Thr Val Asn Leu Thr Cys Asp Thr Pro Glu Glu Asp Asp Ile Thr Trp
305                 310                 315                 320
```

```
Thr Ser Asp Gln Arg His Gly Val Ile Gly Ser Gly Lys Thr Leu Thr
                325                 330                 335

Ile Thr Val Lys Glu Phe Leu Asp Ala Gly Gln Tyr Thr Cys His Lys
                340                 345                 350

Gly Gly Glu Thr Leu Ser His Ser His Leu Leu Leu His Lys Lys Glu
                355                 360                 365

Asn Gly Ile Trp Ser Thr Glu Ile Leu Lys Asn Phe Lys Asn Lys Thr
            370                 375                 380

Phe Leu Lys Cys Glu Ala Pro Asn Tyr Ser Gly Arg Phe Thr Cys Ser
385                 390                 395                 400

Trp Leu Val Gln Arg Asn Met Asp Leu Lys Phe Asn Ile Lys Ser Ser
                405                 410                 415

Ser Ser Pro Pro Asp Ser Arg Ala Val Thr Cys Gly Met Ala Ser Leu
                420                 425                 430

Ser Ala Glu Lys Val Thr Leu Asp Gln Arg Asp Tyr Glu Lys Tyr Ser
            435                 440                 445

Val Ser Cys Gln Glu Asp Val Thr Cys Pro Thr Ala Glu Glu Thr Leu
        450                 455                 460

Pro Ile Glu Leu Ala Leu Glu Ala Arg Gln Gln Asn Lys Tyr Glu Asn
465                 470                 475                 480

Tyr Ser Thr Ser Phe Phe Ile Arg Asp Ile Ile Lys Pro Asp Pro Pro
                485                 490                 495

Lys Asn Leu Gln Met Lys Pro Leu Lys Asn Ser Gln Val Glu Val Ser
                500                 505                 510

Trp Glu Tyr Pro Asp Ser Trp Ser Thr Pro His Ser Tyr Phe Ser Leu
            515                 520                 525

Lys Phe Phe Val Arg Ile Gln Arg Lys Lys Glu Lys Met Lys Glu Thr
            530                 535                 540

Glu Glu Gly Cys Asn Gln Lys Gly Ala Phe Leu Val Glu Lys Thr Ser
545                 550                 555                 560

Thr Glu Val Gln Cys Lys Gly Gly Asn Val Cys Val Gln Ala Gln Asp
                565                 570                 575

Arg Tyr Tyr Asn Ser Ser Cys Ser Lys Trp Ala Cys Val Pro Cys Arg
            580                 585                 590

Val Arg Ser Gly Gly Gly Gly Ser Gly Gly Gly Ser Gly Gly Gly
            595                 600                 605

Gly Ser Arg Val Ile Pro Val Ser Gly Pro Ala Arg Cys Leu Ser Gln
        610                 615                 620

Ser Arg Asn Leu Leu Lys Thr Thr Asp Asp Met Val Lys Thr Ala Arg
625                 630                 635                 640

Glu Lys Leu Lys His Tyr Ser Cys Thr Ala Glu Asp Ile Asp His Glu
                645                 650                 655

Asp Ile Thr Arg Asp Gln Thr Ser Thr Leu Lys Thr Cys Leu Pro Leu
            660                 665                 670

Glu Leu His Lys Asn Glu Ser Cys Leu Ala Thr Arg Glu Thr Ser Ser
            675                 680                 685

Thr Thr Arg Gly Ser Cys Leu Pro Pro Gln Lys Thr Ser Leu Met Met
        690                 695                 700

Thr Leu Cys Leu Gly Ser Ile Tyr Glu Asp Leu Lys Met Tyr Gln Thr
705                 710                 715                 720

Glu Phe Gln Ala Ile Asn Ala Ala Leu Gln Asn His Asn His Gln Gln
                725                 730                 735
```

```
Ile Ile Leu Asp Lys Gly Met Leu Val Ala Ile Asp Glu Leu Met Gln
            740                 745                 750

Ser Leu Asn His Asn Gly Glu Thr Leu Arg Gln Lys Pro Pro Val Gly
            755                 760                 765

Glu Ala Asp Pro Tyr Arg Val Lys Met Lys Leu Cys Ile Leu Leu His
            770                 775                 780

Ala Phe Ser Thr Arg Val Val Thr Ile Asn Arg Val Met Gly Tyr Leu
785                 790                 795                 800

Ser Ser Ala Gly Asp Pro Ala Glu Pro Lys Ser Pro Asp Lys Thr His
            805                 810                 815

Thr Cys Pro Pro Cys Pro Ala Pro Glu Leu Leu Gly Gly Pro Ser Val
            820                 825                 830

Phe Leu Phe Pro Pro Lys Pro Lys Asp Thr Leu Met Ile Ser Arg Thr
            835                 840                 845

Pro Glu Val Thr Cys Val Val Val Asp Val Ser His Glu Asp Pro Glu
            850                 855                 860

Val Lys Phe Asn Trp Tyr Val Asp Gly Val Glu Val His Asn Ala Lys
865                 870                 875                 880

Thr Lys Pro Arg Glu Glu Gln Tyr Asn Ser Thr Tyr Arg Val Val Ser
            885                 890                 895

Val Leu Thr Val Leu His Gln Asp Trp Leu Asn Gly Lys Glu Tyr Lys
            900                 905                 910

Cys Lys Val Ser Asn Lys Ala Leu Pro Ala Pro Ile Glu Lys Thr Ile
            915                 920                 925

Ser Lys Ala Lys Gly Gln Pro Arg Glu Pro Gln Val Tyr Thr Leu Pro
            930                 935                 940

Pro Ser Arg Asp Glu Leu Thr Lys Asn Gln Val Ser Leu Thr Cys Leu
945                 950                 955                 960

Val Lys Gly Phe Tyr Pro Ser Asp Ile Ala Val Glu Trp Glu Ser Asn
            965                 970                 975

Gly Gln Pro Glu Asn Asn Tyr Lys Thr Thr Pro Pro Val Leu Asp Ser
            980                 985                 990

Asp Gly Ser Phe Phe Leu Tyr Ser Lys Leu Thr Val Asp Lys Ser Arg
            995                 1000                1005

Trp Gln Gln Gly Asn Val Phe Ser Cys Ser Val Met His Glu Ala
    1010                1015                1020

Leu His Asn His Tyr Thr Gln Lys Ser Leu Ser Leu Ser Pro Gly
    1025                1030                1035

Lys Lys Asp Pro Lys Phe Trp Val Leu Val Val Val Gly Gly Val
    1040                1045                1050

Leu Ala Cys Tyr Ser Leu Leu Val Thr Val Ala Phe Ile Ile Phe
    1055                1060                1065

Trp Val Arg Ser Lys Arg Ser Arg Leu Leu His Ser Asp Tyr Met
    1070                1075                1080

Asn Met Thr Pro Arg Arg Pro Gly Pro Thr Arg Lys His Tyr Gln
    1085                1090                1095

Ala Tyr Ala Ala Ala Arg Asp Phe Ala Ala Tyr Arg Ser Leu Arg
    1100                1105                1110

Val Lys Phe Ser Arg Ser Ala Asp Ala Pro Ala Tyr Gln Gln Gly
    1115                1120                1125

Gln Asn Gln Leu Tyr Asn Glu Leu Asn Leu Gly Arg Arg Glu Glu
    1130                1135                1140

Tyr Asp Val Leu Asp Lys Arg Arg Gly Arg Asp Pro Glu Met Gly
```

```
                1145                1150                1155
Gly Lys Pro Arg Arg Lys Asn Pro Gln Glu Gly Leu Tyr Asn Glu
        1160                1165                1170
Leu Gln Lys Asp Lys Met Ala Glu Ala Tyr Ser Glu Ile Gly Met
    1175                1180                1185
Lys Gly Glu Arg Arg Arg Gly Lys Gly His Asp Gly Leu Tyr Gln
    1190                1195                1200
Gly Leu Ser Thr Ala Thr Lys Asp Thr Tyr Asp Ala Leu His Met
    1205                1210                1215
Gln Ala Leu Pro Pro Arg
    1220

<210> SEQ ID NO 4
<211> LENGTH: 3675
<212> TYPE: DNA
<213> ORGANISM: artificial sequence
<220> FEATURE:
<223> OTHER INFORMATION: anti-CEA-IL12-CAR (mouse/human)

<400> SEQUENCE: 4
atggattttc aggtgcagat tttcagcttc ctgctaatca gtgcctcagt cataatgtct      60
agaggtgtcc actcccaggt ccaactgcag gagtcaggtc caggtcttgt gagacctagc     120
cagaccctga gcctgacctg caccgtgtct ggcttcacca tcagcagtgg ttatagctgg     180
cactgggtga cagccacc tggacgaggt cttgagtgga ttggatacat acagtacagt       240
ggtatcacta actacaaccc ctctctcaaa agtagagtga caatgctggt agacaccagc     300
aagaaccagt tcagcctgag actcagcagc gtgacagccg ccgacaccgc ggtctattat     360
tgtgcaagag aagactatga ttaccactgg tacttcgatg tctggggcca agggaccacg     420
gtcaccgtct cctcaggagg tggtggatcg ggcggtggcg ggtcgggtgg cggcggatct     480
gacatccagc tgacccagag cccaagcagc ctgagcgcca gcgtgggtga cagagtgacc     540
atcacctgta gtaccagctc gagtgtaagt tacatgcact ggtaccagca aagccaggt     600 aaggctccaa agctgctgat ctacagcaca tccaacctgg cttctggtgt gccaagcaga     660
ttcagcggta gcggtagcgg taccgacttc accttcacca tcagcagcct ccagccagag     720
gacatcgcca cctactactg ccatcagtgg agtagttatc ccacgttcgg ccaagggacc     780
aaggtggaga tcaaagtgga tcccgccgag cccaaatctc tgacaaaaac tcatacatgc     840
ccaccaatgt gggagctgga aaagacgtt tatgttgtag aggtggactg gactcccgat     900 gccccctggag aaacagtgaa cctcacctgt gacacgcctg aagaagatga catcacctgg     960
acctcagacc agagacatgg agtcataggc tctggaaaga ccctgaccat cactgtcaaa    1020
gagtttctag atgctggca gtacacctgc acaaaggag cgagactct gagccactca     1080 catctgctgc tccacaagaa ggaaaatgga atttggtcca ctgaaatttt aaaaatttc    1140 aaaaacaaga ctttcctgaa gtgtgaagca ccaaattact ccggacggtt cacgtgctca    1200
tggctggtgc aaagaaacat ggacttgaag ttcaacatca gagcagtag cagtcccccc    1260 gactctcggg cagtgacatg tggaatggcg tctctgtctg cagagaaggt cacactggac    1320 caaaggact atgagaagta ttcagtgtcc tgccaggaga tgtcacctg cccaactgcc    1380 gaggagaccc tgcccattga actggcgttg gaagcacggc agcagaataa atatgagaac    1440
tacagcacca gcttcttcat cagggacatc atcaaaccag accgcccaa gaacttgcag    1500 atgaagcctt tgaagaactc acaggtggag gtcagctggg agtaccctga ctcctggagc    1560
```

```
actcccatt cctacttctc cctcaagttc tttgttcgaa tccagcgcaa gaaagaaaag    1620
atgaaggaga cagaggaggg gtgtaaccag aaaggtgcgt tcctcgtaga aagacatct    1680 accgaagtcc aatgcaaagg cgggaatgtc tgcgtgcaag ctcaggatcg ctattacaat    1740
tcctcatgca gcaagtgggc atgtgttccc tgcagggtcc gatccggtgg cggtggctcg    1800
ggcggtggtg ggtcgggtgg cggcggatct agggtcattc cagtctctgg acctgccagg    1860
tgtcttagcc agtcccgaaa cctgctgaag accacagatg acatggtgaa gacggccaga    1920
gaaaagctga acattattc ctgcactgct gaagacatcg atcatgaaga catcacacgg    1980 gaccaaaacca gcacattgaa gacctgttta ccactggaac tacacaagaa cgagagttgc    2040
ctggctacta gagagacttc ttccacaaca gagggagct gcctgccccc acagaagacg    2100
tctttgatga tgaccctgtg ccttggtagc atctatgagg acttgaagat gtaccagaca    2160
gagttccagg ccatcaacgc agcacttcag aatcacaacc atcagcagat cattctagac    2220
aagggcatgc tggtggccat cgatgagctg atgcagtctc tgaatcataa tggcgagact    2280
ctgcgccaga aacctcctgt gggagaagca gaccccttaca gagtgaaaat gaagctctgc    2340
atcctgcttc acgccttcag cacccgcgtc gtgaccatca cagggtgat gggctatctg    2400 agctccgccg agatcccgc cgagcccaaa tctcctgaca aaactcacac atgcccaccg    2460
tgcccagcac ctgaactcct ggggggaccg tcagtcttcc tcttccccc aaaacccaag    2520 gacaccctca tgatctcccg gacccctgag gtcacatgcg tggtggtgga cgtgagccac    2580
gaagaccctg aggtcaagtt caactggtac gtggacggcg tggaggtgca taatgccaag    2640
acaaagccgc gggaggagca gtacaacagc acgtaccggg tggtcagcgt cctcaccgtc    2700
ctgcaccagg actggctgaa tggcaaggag tacaagtgca aggtctccaa caaagccctc    2760
ccagccccca tcgagaaaac catctccaaa gccaaagggc agccccgaga accacaggtg    2820
tacaccctgc cccatcccg ggatgagctg accaagaacc aggtcagcct gacctgcctg    2880
gtcaaaggct tctatcccag cgacatcgcc gtggagtggg agagcaatgg gcagccggag    2940
aacaactaca agaccacgcc tcccgtgctg gactccgacg gctccttctt cctctacagc    3000
aagctcaccg tggacaagag caggtggcag caggggaacg tcttctcatg ctccgtgatg    3060
catgaggctc tgcacaacca ctacacgcag aagagcctct ccctgtctcc gggtaaaaaa    3120
gatcccaaat ttgggtgct ggtggtggtt ggtggagtcc tggcttgcta tagcttgcta    3180
gtaacagtgg cctttattat tttctgggtg aggagtaaga ggagcaggct cctgcacagt    3240
gactacatga acatgactcc ccgccgcccc gggcccaccc gcaagcatta ccaggcctat    3300
gccgccgcac gcgacttcgc agcctatcgc tccctgagag tgaagttcag caggagcgca    3360 gacgccccg cgtaccagca gggccagaac cagctctata acgagctcaa tctaggacga    3420
agagaggagt acgatgtttt ggacaagaga cgtggccggg accctgagat gggggggaaag    3480 ccgagaagga gaaccctca ggaaggcct acaatgaac tgcagaaaga taagatggcg    3540
gaggcctaca gtgagattgg gatgaaaggc gagcgccgga ggggcaaggg gcacgatggc    3600
ctttaccagg gtctcagtac agccaccaag gacacctacg acgcccttca catgcaggcc    3660 ctgcccctc gctaa                                                      3675

<210> SEQ ID NO 5
<211> LENGTH: 3738
<212> TYPE: DNA
<213> ORGANISM: Artificial sequence
<220> FEATURE:
<223> OTHER INFORMATION: C595scFv-mIL12-Fc-dCD28zeta CAR
```

(anti-Muc1-IL12-CAR)

\<400\> SEQUENCE: 5

```
atggattttc aggtgcagat tttcagcttc ctgctaatca gtgcctcagt cataatgtct      60
agaatggccc aggtccaact gcaggagtca gggggaggct tagtgcagcc tggagggtcc     120
ctgaaactct cctgtgcagc ctctggattc actttcagta gctatggcat gtcttgggtt     180
cgccagactc cagacaagag gctggagttg gtcgcaacca ttaatagtaa tggtggtagc     240
acctattatc cagacagtgt gaagggccga ttcaccatct ccagagacaa tgccaagaac     300
accctgtacc tgcaaatgag cagtctgaag tctgaggaca gccatgtgta ttactgtgca     360
agagatcggg atggttacga cgagggattt gactactggg gccaaggcac cacggtcacc     420
gtctcctcag gtggaggcgg ttcaggcgga ggtggctctg gcggtggcgg atcggacatc     480
gagctcactc agtctccatc aatcatgtct gcatctccag gggagaaggt caccatgacc     540
tgcagtgcca gctcaagtgt aagttacatg cactggtacc agcagaagtc aggcacctcc     600
cccaaaagat ggatttatga cacatccaaa ctggcttctg gagtccctgc tcgcttcagt     660
ggcagtgggt ctgggacctc ttactctctc acaatcagca gcatggaggc tgaagatgct     720
gccacttatt actgccagca gtggagtagt aacccaccca cgctcggacg gaggacccag     780
ctgcagctga acgggcgga tcccgccgag cccaaatctc ctgacaaaac tcacacatgc     840
ccaatgggtc ctcagaagct aaccatctcc tggtttgcca tcgttttgct ggtgtctcca     900
ctcatggcca tgtgggagct ggagaaagac gtttatgttg tagaggtgga ctggactccc     960
gatgcccctg gagaaacagt gaacctcacc tgtgacacgc tgaagaaga tgacatcacc    1020
tggacctcag accagagaca tggagtcata ggctctggaa agaccctgac catcactgtc    1080
aaagagtttc tagatgctgg ccagtacacc tgccacaaag aggcgagac tctgagccac    1140
tcacatctgc tgctccacaa gaaggaaaat ggaatttggt ccactgaaat tttaaaaaat    1200
ttcaaaaaca gacttttcct gaagtgtgaa gcaccaaatt actccggacg gttcacgtgc    1260
tcatggctgg tgcaaagaaa catggacttg aagttcaaca tcaagagcag tagcagtccc    1320
cccgactctc gggcagtgac atgtggaatg gcgtctctgt ctgcagagaa ggtcacactg    1380
gaccaaaggg actatgagaa gtattcagtg tcctgcctgg aggatgtcac ctgcccaact    1440
gccgaggaga ccctgcccat tgaactggcg ttggaagcac ggcagcagaa taaatatgag    1500
aactacagca ccagcttctt catcagggac atcatcaaac cagaccgcc aagaacttg    1560
cagatgaagc tttgaagaa ctcacaggtg aggtcagct gggagtaccc tgactcctgg    1620
agcactcccc attcctactt ctccctcaag ttctttgttc gaatccagcg caagaaagaa    1680
aagatgaagg agacagagga gggtgtaac cagaaaggtg cgttcctcgt agagaagaca    1740
tctaccgaag tccaatgcaa aggcgggaat gtctgcgtgc aagctcagga tcgctattac    1800
aattcctcat gcagcaagtg gcatgtgtt ccctgcaggg tccgatccgg tggcggtggc    1860
tcgggcggtg gtgggtcggg tggcggcgga tctagggtca ttccagtctc tggacctgcc    1920
aggtgtctta gccagtcccg aaacctgctg aagaccacag atgacatggt gaagacggcc    1980
agagaaaagc tgaaacatta ttcctgcact gctgaagaca tcgatcatga agacatcaca    2040
cgggaccaaa ccagcacatt gaagacctgt ttaccactgg aactacacaa gaacgagagt    2100
tgcctggcta ctagagagac ttcttccaca caagaggga gctgcctgcc ccacagaag    2160
acgtctttga tgatgaccct gtgccttggt agcatctatg aggacttgaa gatgtaccag    2220
acagagttcc aggccatcaa cgcagcactt cagaatcaca accatcagca gatcattcta    2280
```

```
gacaagggca tgctggtggc catcgatgag ctgatgcagt ctctgaatca taatggcgag    2340
actctgcgcc agaaacctcc tgtgggagaa gcagacccct tacagagtga aatgaagctc    2400
tgcatcctgc ttcacgcctt cagcacccgc gtcgtgacca tcaacagggt gatgggctat    2460
ctgagctccg ccggagatcc cgccgagccc aaatctcctg acaaaactca catgcccca    2520 ccgtgcccag cacctgaact cctgggggga ccgtcagtct tcctcttccc cccaaaaccc    2580
aaggacaccc tcatgatctc ccggacccct gaggtcacat gcgtggtggt ggacgtgagc    2640
cacgaagacc ctgaggtcaa gttcaactgg tacgtggacg gcgtggaggt gcataatgcc    2700
aagacaaagc cgcggggagga gcagtacaac agcacgtacc gggtggtcag cgtcctcacc    2760
gtcctgcacc aggactggct gaatggcaag gagtacaagt gcaaggtctc caacaaagcc    2820
ctcccagccc ccatcgagaa aaccatctcc aaagccaaag gcagccccg agaaccacag    2880 gtgtacaccc tgcccccatc ccgggatgag ctgaccaaga accaggtcag cctgacctgc    2940
ctggtcaaag gcttctatcc cagcgacatc gccgtggagt gggagagcaa tgggcagccg    3000
gagaacaact acaagaccac gcctcccgtg ctggactccg acggctcctt cttcctctac    3060
agcaagctca ccgtggacaa gagcaggtgg cagcagggga acgtcttctc atgctccgtg    3120
atgcatgagg ctctgcacaa ccactacacg cagaagagcc tctccctgtc tccgggtaaa    3180
aaagatccca atttttgggt gctggtggtg gttggtggag tcctggcttg ctatagcttg    3240
ctagtaacag tggcctttat tattttctgg gtgaggagta agaggagcag gctcctgcac    3300
agtgactaca tgaacatgac tccccgccgc cccgggccca cccgcaagca ttaccaggcc    3360
tatgccgccg cacgcgactt cgcagcctat cgctccctga gtgaagtt cagcaggagc    3420 gcagacgccc ccgcgtacca gcagggccag aaccagctct ataacgagct caatctagga    3480
cgaagagagg agtacgatgt tttggacaag agacgtggcc gggaccctga tgggggga    3540 aagccgagaa ggaagaaccc tcaggaaggc ctgtacaatg aactcagaa agataagatg    3600 gcggaggcct acagtgagat tgggatgaaa ggcgagcgcc ggagggcaa ggggcacgat    3660 ggcctttacc agggtctcag tacagccacc aaggacacct cgacgccct tcacatgcag    3720 gccctgcccc tcgctaa                                                  3738
```

<210> SEQ ID NO 6
<211> LENGTH: 1246
<212> TYPE: PRT
<213> ORGANISM: Artificial sequence
<220> FEATURE:
<223> OTHER INFORMATION: C595scFv-mIL12-Fc-dCD28zeta
      (anti-Muc1-IL12-CAR)

<400> SEQUENCE: 6

Met Asp Phe Gln Val Gln Ile Phe Ser Phe Leu Leu Ile Ser Ala Ser
1               5                   10                  15

Val Ile Met Ser Arg Met Ala Gln Val Gln Leu Gln Glu Ser Gly Gly
            20                  25                  30

Gly Leu Val Gln Pro Gly Gly Ser Leu Lys Leu Ser Cys Ala Ala Ser
        35                  40                  45

Gly Phe Thr Phe Ser Ser Tyr Gly Met Ser Trp Val Arg Gln Thr Pro
    50                  55                  60

Asp Lys Arg Leu Glu Leu Val Ala Thr Ile Asn Ser Asn Gly Gly Ser
65                  70                  75                  80

Thr Tyr Tyr Pro Asp Ser Val Lys Gly Arg Phe Thr Ile Ser Arg Asp
                85                  90                  95

```
Asn Ala Lys Asn Thr Leu Tyr Leu Gln Met Ser Ser Leu Lys Ser Glu
            100                 105                 110

Asp Thr Ala Met Tyr Tyr Cys Ala Arg Asp Arg Asp Gly Tyr Asp Glu
            115                 120                 125

Gly Phe Asp Tyr Trp Gly Gln Gly Thr Thr Val Thr Val Ser Ser Gly
            130                 135                 140

Gly Gly Gly Ser Gly Gly Gly Ser Gly Gly Gly Ser Asp Ile
145                 150                 155                 160

Glu Leu Thr Gln Ser Pro Ser Ile Met Ser Ala Ser Pro Gly Glu Lys
                165                 170                 175

Val Thr Met Thr Cys Ser Ala Ser Ser Val Ser Tyr Met His Trp
            180                 185                 190

Tyr Gln Gln Lys Ser Gly Thr Ser Pro Lys Arg Trp Ile Tyr Asp Thr
            195                 200                 205

Ser Lys Leu Ala Ser Gly Val Pro Ala Arg Phe Ser Gly Ser Gly Ser
    210                 215                 220

Gly Thr Ser Tyr Ser Leu Thr Ile Ser Ser Met Glu Ala Glu Asp Ala
225                 230                 235                 240

Ala Thr Tyr Tyr Cys Gln Gln Trp Ser Ser Asn Pro Pro Thr Leu Gly
            245                 250                 255

Arg Arg Thr Gln Leu Gln Leu Lys Arg Ala Asp Pro Ala Glu Pro Lys
            260                 265                 270

Ser Pro Asp Lys Thr His Thr Cys Pro Met Gly Pro Gln Lys Leu Thr
            275                 280                 285

Ile Ser Trp Phe Ala Ile Val Leu Leu Val Ser Pro Leu Met Ala Met
            290                 295                 300

Trp Glu Leu Glu Lys Asp Val Tyr Val Val Glu Val Asp Trp Thr Pro
305                 310                 315                 320

Asp Ala Pro Gly Glu Thr Val Asn Leu Thr Cys Asp Thr Pro Glu Glu
            325                 330                 335

Asp Asp Ile Thr Trp Thr Ser Asp Gln Arg His Gly Val Ile Gly Ser
            340                 345                 350

Gly Lys Thr Leu Thr Ile Thr Val Lys Glu Phe Leu Asp Ala Gly Gln
            355                 360                 365

Tyr Thr Cys His Lys Gly Gly Glu Thr Leu Ser His Ser His Leu Leu
            370                 375                 380

Leu His Lys Lys Glu Asn Gly Ile Trp Ser Thr Glu Ile Leu Lys Asn
385                 390                 395                 400

Phe Lys Asn Lys Thr Phe Leu Lys Cys Glu Ala Pro Asn Tyr Ser Gly
                405                 410                 415

Arg Phe Thr Cys Ser Trp Leu Val Gln Arg Asn Met Asp Leu Lys Phe
            420                 425                 430

Asn Ile Lys Ser Ser Ser Ser Pro Asp Ser Arg Ala Val Thr Cys
            435                 440                 445

Gly Met Ala Ser Leu Ser Ala Glu Lys Val Thr Leu Asp Gln Arg Asp
            450                 455                 460

Tyr Glu Lys Tyr Ser Val Ser Cys Leu Glu Asp Val Thr Cys Pro Thr
465                 470                 475                 480

Ala Glu Glu Thr Leu Pro Ile Glu Leu Ala Leu Glu Ala Arg Gln Gln
                485                 490                 495

Asn Lys Tyr Glu Asn Tyr Ser Thr Ser Phe Phe Ile Arg Asp Ile Ile
            500                 505                 510
```

-continued

```
Lys Pro Asp Pro Pro Lys Asn Leu Gln Met Lys Pro Leu Lys Asn Ser
        515                 520                 525
Gln Val Glu Val Ser Trp Glu Tyr Pro Asp Ser Trp Ser Thr Pro His
        530                 535                 540
Ser Tyr Phe Ser Leu Lys Phe Phe Val Arg Ile Gln Arg Lys Lys Glu
545                 550                 555                 560
Lys Met Lys Glu Thr Glu Gly Cys Asn Gln Lys Gly Ala Phe Leu
                565                 570                 575
Val Glu Lys Thr Ser Thr Glu Val Gln Cys Lys Gly Asn Val Cys
                580                 585                 590
Val Gln Ala Gln Asp Arg Tyr Tyr Asn Ser Ser Cys Ser Lys Trp Ala
        595                 600                 605
Cys Val Pro Cys Arg Val Arg Ser Gly Gly Gly Ser Gly Gly Gly
        610                 615                 620
Gly Ser Gly Gly Gly Gly Ser Arg Val Ile Pro Val Ser Gly Pro Ala
625                 630                 635                 640
Arg Cys Leu Ser Gln Ser Arg Asn Leu Leu Lys Thr Thr Asp Asp Met
                645                 650                 655
Val Lys Thr Ala Arg Glu Lys Leu Lys His Tyr Ser Cys Thr Ala Glu
                660                 665                 670
Asp Ile Asp His Glu Asp Ile Thr Arg Asp Gln Thr Ser Thr Leu Lys
                675                 680                 685
Thr Cys Leu Pro Leu Glu Leu His Lys Asn Glu Ser Cys Leu Ala Thr
        690                 695                 700
Arg Glu Thr Ser Ser Thr Thr Arg Gly Ser Cys Leu Pro Pro Gln Lys
705                 710                 715                 720
Thr Ser Leu Met Met Thr Leu Cys Leu Gly Ser Ile Tyr Glu Asp Leu
                725                 730                 735
Lys Met Tyr Gln Thr Glu Phe Gln Ala Ile Asn Ala Ala Leu Gln Asn
                740                 745                 750
His Asn His Gln Gln Ile Ile Leu Asp Lys Gly Met Leu Val Ala Ile
        755                 760                 765
Asp Glu Leu Met Gln Ser Leu Asn His Asn Gly Glu Thr Leu Arg Gln
        770                 775                 780
Lys Pro Pro Val Gly Glu Ala Asp Pro Tyr Arg Val Lys Met Lys Leu
785                 790                 795                 800
Cys Ile Leu Leu His Ala Phe Ser Thr Arg Val Val Thr Ile Asn Arg
                805                 810                 815
Val Met Gly Tyr Leu Ser Ser Ala Gly Asp Pro Ala Glu Pro Lys Ser
                820                 825                 830
Pro Asp Lys Thr His Thr Cys Pro Pro Cys Pro Ala Pro Glu Leu Leu
        835                 840                 845
Gly Gly Pro Ser Val Phe Leu Phe Pro Pro Lys Pro Lys Asp Thr Leu
        850                 855                 860
Met Ile Ser Arg Thr Pro Glu Val Thr Cys Val Val Val Asp Val Ser
865                 870                 875                 880
His Glu Asp Pro Glu Val Lys Phe Asn Trp Tyr Val Asp Gly Val Glu
                885                 890                 895
Val His Asn Ala Lys Thr Lys Pro Arg Glu Glu Gln Tyr Asn Ser Thr
                900                 905                 910
Tyr Arg Val Val Ser Val Leu Thr Val Leu His Gln Asp Trp Leu Asn
        915                 920                 925
Gly Lys Glu Tyr Lys Cys Lys Val Ser Asn Lys Ala Leu Pro Ala Pro
```

```
                930           935           940
Ile Glu Lys Thr Ile Ser Lys Ala Lys Gly Gln Pro Arg Glu Pro Gln
945           950               955               960
Val Tyr Thr Leu Pro Pro Ser Arg Asp Glu Leu Thr Lys Asn Gln Val
                965               970               975
Ser Leu Thr Cys Leu Val Lys Gly Phe Tyr Pro Ser Asp Ile Ala Val
            980               985               990
Glu Trp Glu Ser Asn Gly Gln Pro Glu Asn Asn Tyr Lys Thr Thr Pro
            995               1000              1005
Pro Val Leu Asp Ser Asp Gly Ser Phe Phe Leu Tyr Ser Lys Leu
    1010              1015              1020
Thr Val Asp Lys Ser Arg Trp Gln Gln Gly Asn Val Phe Ser Cys
    1025              1030              1035
Ser Val Met His Glu Ala Leu His Asn His Tyr Thr Gln Lys Ser
    1040              1045              1050
Leu Ser Leu Ser Pro Gly Lys Lys Asp Pro Lys Phe Trp Val Leu
    1055              1060              1065
Val Val Val Gly Gly Val Leu Ala Cys Tyr Ser Leu Leu Val Thr
    1070              1075              1080
Val Ala Phe Ile Ile Phe Trp Val Arg Ser Lys Arg Ser Arg Leu
    1085              1090              1095
Leu His Ser Asp Tyr Met Asn Met Thr Pro Arg Arg Pro Gly Pro
    1100              1105              1110
Thr Arg Lys His Tyr Gln Ala Tyr Ala Ala Ala Arg Asp Phe Ala
    1115              1120              1125
Ala Tyr Arg Ser Leu Arg Val Lys Phe Ser Arg Ser Ala Asp Ala
    1130              1135              1140
Pro Ala Tyr Gln Gln Gly Gln Asn Gln Leu Tyr Asn Glu Leu Asn
    1145              1150              1155
Leu Gly Arg Arg Glu Glu Tyr Asp Val Leu Asp Lys Arg Arg Gly
    1160              1165              1170
Arg Asp Pro Glu Met Gly Gly Lys Pro Arg Arg Lys Asn Pro Gln
    1175              1180              1185
Glu Gly Leu Tyr Asn Glu Leu Gln Lys Asp Lys Met Ala Glu Ala
    1190              1195              1200
Tyr Ser Glu Ile Gly Met Lys Gly Glu Arg Arg Arg Gly Lys Gly
    1205              1210              1215
His Asp Gly Leu Tyr Gln Gly Leu Ser Thr Ala Thr Lys Asp Thr
    1220              1225              1230
Tyr Asp Ala Leu His Met Gln Ala Leu Pro Pro Arg Glx
    1235              1240              1245

<210> SEQ ID NO 7
<211> LENGTH: 63
<212> TYPE: DNA
<213> ORGANISM: Artificial sequence
<220> FEATURE:
<223> OTHER INFORMATION: Lkappa leader

<400> SEQUENCE: 7 atggatttc aggtgcagat tttcagcttc ctgctaatca gtgcctcagt cataatgtct     60
aga                                                                  63

<210> SEQ ID NO 8
<211> LENGTH: 735
```

```
<212> TYPE: DNA
<213> ORGANISM: Artificial sequence
<220> FEATURE:
<223> OTHER INFORMATION: anti-Muc1 scFv C595

<400> SEQUENCE: 8
atggcccagg tccaactgca ggagtcaggg ggaggcttag tgcagcctgg agggtccctg      60
aaactctcct gtgcagcctc tggattcact ttcagtagct atggcatgtc ttgggttcgc     120
cagactccag acaagaggct ggagttggtc gcaaccatta atagtaatgg tggtagcacc     180
tattatccag acagtgtgaa gggccgattc accatctcca gagacaatgc caagaacacc     240
ctgtacctgc aaatgagcag tctgaagtct gaggacacac catgtatta ctgtgcaaga     300 gatcgggatg gttacgacga gggatttgac tactggggcc aaggcaccac ggtcaccgtc     360
tcctcaggtg gaggcggttc aggcggaggt ggctctggcg gtggcggatc ggacatcgag     420
ctcactcagt ctccatcaat catgtctgca tctccagggg agaaggtcac catgacctgc     480
agtgccagct caagtgtaag ttacatgcac tggtaccagc agaagtcagg cacctccccc     540
aaaagatgga tttatgacac atccaaactg gcttctggag tccctgctcg cttcagtggc     600
agtgggtctg ggacctctta ctctctcaca atcagcagca tggaggctga agatgctgcc     660
acttattact gccagcagtg gagtagtaac ccacccacgc tcggacggag gacccagctg     720
cagctgaaac gggcg                                                      735

<210> SEQ ID NO 9
<211> LENGTH: 1632
<212> TYPE: DNA
<213> ORGANISM: Artificial sequence
<220> FEATURE:
<223> OTHER INFORMATION: mouse single chain IL12 (mscIL12)

<400> SEQUENCE: 9
atgggtcctc agaagctaac catctcctgg tttgccatcg ttttgctggt gtctccactc      60
atggccatgt gggagctgga aaagacgtt tatgttgtag aggtggactg gactcccgat     120
gcccctggag aaacagtgaa cctcacctgt gacacgcctg aagaagatga catcacctgg     180
acctcagacc agagacatgg agtcataggc tctggaaaga ccctgaccat cactgtcaaa     240
gagtttctag atgctggcca gtacacctgc cacaaggag gcgagactct gagccactca     300
catctgctgc tccacaagaa ggaaaatgga atttggtcca ctgaaatttt aaaaaatttc     360
aaaaacaaga ctttcctgaa gtgtgaagca ccaaattact ccggacggtt cacgtgctca     420
tggctggtgc aaagaaacat ggacttgaag ttcaacatca gagcagtag cagtccccc     480 gactctcggg cagtgacatg tggaatggcg tctctgtctg cagagaaggt cacactggac     540
caaagggact atgagaagta ttcagtgtcc tgcctggagg atgtcacctg cccaactgcc     600
gaggagaccc tgcccattga actggcgttg gaagcacggc agcagaataa atatgagaac     660
tacagcacca gcttcttcat cagggacatc atcaaaccag accgcccaa gaacttgcag     720 atgaagcctt tgaagaactc acaggtggag gtcagctggg agtaccctga ctcctggagc     780 actcccccatt cctacttctc cctcaagttc tttgttcgaa tccagcgcaa gaaagaaaag     840
atgaaggaga cagaggaggg gtgtaaccag aaaggtgcgt tcctcgtaga aaagacatct     900
accgaagtcc aatgcaaagg cgggaatgtc tgcgtgcaag ctcaggatcg ctattacaat     960
tcctcatgca gcaagtgggc atgtgttccc tgcagggtcc gatccggtgg cggtggctcg    1020
ggcggtggtg ggtcgggtgg cggcggatct agggtcattc cagtctctgg acctgccagg    1080
```

```
tgtcttagcc agtcccgaaa cctgctgaag accacagatg acatggtgaa gacggccaga    1140
gaaaagctga acattattc ctgcactgct gaagacatcg atcatgaaga catcacacgg     1200
gaccaaacca gcacattgaa gacctgttta ccactggaac tacacaagaa cgagagttgc    1260
ctggctacta gagagacttc ttccacaaca gagggagct gcctgccccc acagaagacg     1320
tctttgatga tgaccctgtg ccttggtagc atctatgagg acttgaagat gtaccagaca    1380
gagttccagg ccatcaacgc agcacttcag aatcacaacc atcagcagat cattctagac    1440
aagggcatgc tggtggccat cgatgagctg atgcagtctc tgaatcataa tggcgagact    1500
ctgcgccaga aacctcctgt gggagaagca gaccccttaca gagtgaaaat gaagctctgc    1560
atcctgcttc acgccttcag caccgcgtc gtgaccatca caggtgat gggctatctg       1620 agctccgccg ga                                                        1632

<210> SEQ ID NO 10
<211> LENGTH: 45
<212> TYPE: DNA
<213> ORGANISM: Artificial sequence
<220> FEATURE:
<223> OTHER INFORMATION: human IgG-Hinge region

<400> SEQUENCE: 10
gatcccgccg agcccaaatc tcctgacaaa actcacacat gccca                    45

<210> SEQ ID NO 11
<211> LENGTH: 1263
<212> TYPE: DNA
<213> ORGANISM: Artificial sequence
<220> FEATURE:
<223> OTHER INFORMATION: human IgG-Fc-CD28dlckzeta

<400> SEQUENCE: 11
gatcccgccg agcccaaatc tcctgacaaa actcacacat gcccaccgtg cccagcacct    60
gaactcctgg gggaccgtc agtcttcctc ttccccccaa acccaagga cacctcatg       120 atctcccgga cccctgaggt cacatgcgtg gtggtggacg tgagccacga agaccctgag    180
gtcaagttca actggtacgt ggacggcgtg gaggtgcata atgccaagac aaagccgcgg    240
gaggagcagt acaacagcac gtaccgggtg gtcagcgtcc tcaccgtcct gcaccaggac    300
tggctgaatg gcaaggagta caagtgcaag gtctccaaca aagcccctcc agcccccatc    360
gagaaaacca tctccaaagc caaagggcag ccccgagaac cacaggtgta caccctgccc    420
ccatcccggg atgagctgac caagaaccag gtcagcctga cctgcctggt caaaggcttc    480
tatcccagcg acatcgccgt ggagtgggag agcaatgggc agccggagaa caactacaag    540
accacgcctc ccgtgctgga ctccgacggc tccttcttcc tctacagcaa gctcaccgtg    600
gacaagagca ggtggcagca ggggaacgtc ttctcatgct ccgtgatgca tgaggctctg    660
cacaaccact acacgcagaa gagcctctcc ctgtctccgg gtaaaaaaga tcccaaattt    720
tgggtgctgg tggtggttgg tggagtcctg gcttgctata gcttgctagt aacagtggcc    780
tttattattt tctgggtgag gagtaagagg agcaggctcc tgcacagtga ctacatgaac    840
atgactcccc gccgcccgg gcccaccgc aagcattacc aggcctatgc cgccgcacgc      900
gacttcgcag cctatcgctc cctgagagtg aagttcagca ggagcgcaga cgcccccgcg    960
taccagcagg gccagaacca gctctataac gagctcaatc taggacgaag agaggagtac    1020 gatgttttg acaagagacg tggccgggac cctgagatgg gggaaagcc gagaaggaag     1080 aaccctcagg aaggcctgta caatgaactg cagaaagata agatggcgga ggcctacagt    1140
```

```
gagattggga tgaaaggcga gcgccggagg ggcaagggggc acgatggcct ttaccagggt    1200
ctcagtacag ccaccaagga cacctacgac gcccttcaca tgcaggccct gcccctcgc     1260 taa                                                                   1263
```

<210> SEQ ID NO 12
<211> LENGTH: 2574
<212> TYPE: DNA
<213> ORGANISM: Artificial sequence
<220> FEATURE:
<223> OTHER INFORMATION: mIL7-BW431/26scFv-Fc-dCD28zeta CAR
      (IL7-anti-CEA-CAR)

<400> SEQUENCE: 12

```
atggattttc aggtgcagat tttcagcttc ctgctaatca gtgcctcagt cataatgtct     60
agagagtgcc acattaaaga caaagaaggt aaagcatatg agagtgtact gatgatcagc    120
atcgatgaat tggacaaaat gacaggaact gatagtaatt gcccgaataa tgaaccaaac    180 tttttagaa aacatgtatg tgatgataca aaggaagctg ctttctaaa tcgtgctgct     240 cgcaagttga agcaatttct taaaatgaat atcagtgaag aattcaatgt ccacttacta    300
acagtatcac aaggcacaca aacactggtg aactgcacga gtaaggaaga aaaaacgta    360 aaggaacaga aaagaatga tgcatgtttc ctaaagagac tactgagaga aataaaaact    420
tgttggaata aaattttgaa gggcagtata gcggccgcag gaggcggggg ttctggtgga    480
ggcggaagcg gtggcggggg ttcaggaggc ggggttccg gtggtggcgg cagtggtggt    540
ggcggcagtg gtggtggcgg cagtggtggt ggcggcagtg gtgtccactc ccaggtccaa    600
ctgcaggagt caggtccagg tcttgtgaga cctagccaga ccctgagcct gacctgcacc    660
gtgtctggct tcaccatcag cagtggttat agctggcact gggtgagaca gccacctgga    720
cgaggtcttg agtggattgg atacatacag tacagtggta tcactaacta caacccctct    780
ctcaaaagta gagtgacaat gctggtagac accagcaaga accagttcag cctgagactc    840
agcagcgtga cagccgccga caccgcggtc tattattgtg caagagaaga ctatgattac    900
cactggtact cgatgtctg gggccaaggg accacggtca ccgtctcctc aggaggtggt    960
ggatcgggcg gtggcgggtc gggtggcggc ggatctgaca tccagctgac ccagagccca   1020
agcagcctga cgccagcgt gggtgacaga gtgaccatca cctgtagtac cagctcgagt    1080
gtaagttaca tgcactggta ccagcagaag ccaggtaagg ctccaaagct gctgatctac    1140
agcacatcca acctggcttc tggtgtgcca agcagattca gcggtagcgg tagcggtacc    1200 gacttcaccct tcaccatcag cagcctccag ccagaggaca tcgccaccta ctactgccat   1260
cagtggagta gttatcccac gttcggccaa gggaccaagg tggagatcaa agtggatccc    1320
gccgagccca atctcctga caaaactcac acatgcccac cgtgcccagc acctccagtc    1380
gcgggaccgt cagtcttcct cttccccccca aaacccaagg acaccctcat gatcgcccgg    1440
acccctgagg tcacatgcgt ggtggtggac gtgagccacg aagaccctga ggtcaagttc    1500
aactggtacg tggacggcgt ggaggtgcat aatgccaaga caaagccgcg ggaggagcag    1560
tacaacagca cgtaccgtgt ggtcagcgtc ctcaccgtcc tgcaccagga ctggctgaat    1620
ggcaaggagt acaagtgcaa ggtctccaac aaagccctcc cagcccccat cgagaaaacc    1680
atctccaaag ccaaagggca gccccgagaa ccacaggtgt acaccctgcc cccatcccgg    1740
gatgagctga ccaagaacca ggtcagcctg acctgcctgg tcaaaggctt ctatcccagc    1800
gacatcgccg tggagtggga gagcaatggg cagccggaga caactacaa gaccacgcct    1860
```

```
cccgtgctgg actccgacgg ctccttcttc ctctacagca agctcaccgt ggacaagagc    1920
aggtggcagc aggggaacgt cttctcatgc tccgtgatgc atgaggctct gcacaaccac    1980
tacacgcaga agagcctctc cctgtctccg ggtaaaaaag atcccaaatt ttgggtgctg    2040
gtggtggttg gtggagtcct ggcttgctat agcttgctag taacagtggc ctttattatt    2100
ttctgggtga ggagtaagag gagcaggctc ctgcacagtg actacatgaa catgactccc    2160
cgccgccccg ggcccacccg caagcattac caggcctatg ccgccgcacg cgacttcgca    2220
gcctatcgct ccctgagagt gaagttcagc aggagcgcag acgcccccgc gtaccagcag    2280
ggccagaacc agctctataa cgagctcaat ctaggacgaa gagaggagta cgatgttttg    2340
gacaagagac gtggccggga ccctgagatg gggggaaagc cgagaaggaa gaaccctcag    2400
gaaggcctgt acaatgaact gcagaaagat aagatggcgg aggcctacag tgagattggg    2460
atgaaaggcg agcgccggag gggcaagggg cacgatggcc tttaccaggg tctcagtaca    2520
gccaccaagg acacctacga cgcccttcac atgcaggccc tgccccctcg ctaa          2574
```

<210> SEQ ID NO 13
<211> LENGTH: 858
<212> TYPE: PRT
<213> ORGANISM: Artificial sequence
<220> FEATURE:
<223> OTHER INFORMATION: mIL7-BW431/26scFv-Fc-dCD28zeta CAR
      (IL7-anti-CEA-CAR)

<400> SEQUENCE: 13

```
Met Asp Phe Gln Val Gln Ile Phe Ser Phe Leu Leu Ile Ser Ala Ser
1               5                   10                  15

Val Ile Met Ser Arg Glu Cys His Ile Lys Asp Lys Glu Gly Lys Ala
            20                  25                  30

Tyr Glu Ser Val Leu Met Ile Ser Ile Asp Glu Leu Asp Lys Met Thr
        35                  40                  45

Gly Thr Asp Ser Asn Cys Pro Asn Asn Glu Pro Asn Phe Phe Arg Lys
    50                  55                  60

His Val Cys Asp Asp Thr Lys Glu Ala Ala Phe Leu Asn Arg Ala Ala
65                  70                  75                  80

Arg Lys Leu Lys Gln Phe Leu Lys Met Asn Ile Ser Glu Glu Phe Asn
                85                  90                  95

Val His Leu Leu Thr Val Ser Gln Gly Thr Gln Thr Leu Val Asn Cys
            100                 105                 110

Thr Ser Lys Glu Glu Lys Asn Val Lys Glu Gln Lys Lys Asn Asp Ala
        115                 120                 125

Cys Phe Leu Lys Arg Leu Leu Arg Glu Ile Lys Thr Cys Trp Asn Lys
    130                 135                 140

Ile Leu Lys Gly Ser Ile Ala Ala Ala Gly Gly Gly Ser Gly Gly
145                 150                 155                 160

Gly Gly Ser Gly Gly Gly Gly Ser Gly Gly Gly Gly Ser Gly Gly Gly
                165                 170                 175

Gly Ser Gly Gly Gly Gly Ser Gly Gly Gly Gly Ser Gly Gly Gly Gly
            180                 185                 190

Ser Gly Val His Ser Gln Val Gln Leu Gln Glu Ser Gly Pro Gly Leu
        195                 200                 205

Val Arg Pro Ser Gln Thr Leu Ser Leu Thr Cys Thr Val Ser Gly Phe
    210                 215                 220

Thr Ile Ser Ser Gly Tyr Ser Trp His Trp Val Arg Gln Pro Pro Gly
```

-continued

```
                225                 230                 235                 240
Arg Gly Leu Glu Trp Ile Gly Tyr Ile Gln Tyr Ser Gly Ile Thr Asn
                    245                 250                 255
Tyr Asn Pro Ser Leu Lys Ser Arg Val Thr Met Leu Val Asp Thr Ser
            260                 265                 270
Lys Asn Gln Phe Ser Leu Arg Leu Ser Ser Val Thr Ala Ala Asp Thr
        275                 280                 285
Ala Val Tyr Tyr Cys Ala Arg Glu Asp Tyr Asp Tyr His Trp Tyr Phe
    290                 295                 300
Asp Val Trp Gly Gln Gly Thr Thr Val Thr Val Ser Ser Gly Gly Gly
305                 310                 315                 320
Gly Ser Gly Gly Gly Gly Ser Gly Gly Gly Gly Ser Asp Ile Gln Leu
                325                 330                 335
Thr Gln Ser Pro Ser Ser Leu Ser Ala Ser Val Gly Asp Arg Val Thr
            340                 345                 350
Ile Thr Cys Ser Thr Ser Ser Val Ser Tyr Met His Trp Tyr Gln
        355                 360                 365
Gln Lys Pro Gly Lys Ala Pro Lys Leu Leu Ile Tyr Ser Thr Ser Asn
    370                 375                 380
Leu Ala Ser Gly Val Pro Ser Arg Phe Ser Gly Ser Gly Ser Gly Thr
385                 390                 395                 400
Asp Phe Thr Phe Thr Ile Ser Ser Leu Gln Pro Glu Asp Ile Ala Thr
                405                 410                 415
Tyr Tyr Cys His Gln Trp Ser Ser Tyr Pro Thr Phe Gly Gln Gly Thr
            420                 425                 430
Lys Val Glu Ile Lys Val Asp Pro Ala Glu Pro Lys Ser Pro Asp Lys
        435                 440                 445
Thr His Thr Cys Pro Pro Cys Pro Ala Pro Val Ala Gly Pro Ser
    450                 455                 460
Val Phe Leu Phe Pro Pro Lys Pro Lys Asp Thr Leu Met Ile Ala Arg
465                 470                 475                 480
Thr Pro Glu Val Thr Cys Val Val Val Asp Val Ser His Glu Asp Pro
                485                 490                 495
Glu Val Lys Phe Asn Trp Tyr Val Asp Gly Val Glu Val His Asn Ala
            500                 505                 510
Lys Thr Lys Pro Arg Glu Glu Gln Tyr Asn Ser Thr Tyr Arg Val Val
        515                 520                 525
Ser Val Leu Thr Val Leu His Gln Asp Trp Leu Asn Gly Lys Glu Tyr
    530                 535                 540
Lys Cys Lys Val Ser Asn Lys Ala Leu Pro Ala Pro Ile Glu Lys Thr
545                 550                 555                 560
Ile Ser Lys Ala Lys Gly Gln Pro Arg Glu Pro Gln Val Tyr Thr Leu
                565                 570                 575
Pro Pro Ser Arg Asp Glu Leu Thr Lys Asn Gln Val Ser Leu Thr Cys
            580                 585                 590
Leu Val Lys Gly Phe Tyr Pro Ser Asp Ile Ala Val Glu Trp Glu Ser
        595                 600                 605
Asn Gly Gln Pro Glu Asn Asn Tyr Lys Thr Thr Pro Pro Val Leu Asp
    610                 615                 620
Ser Asp Gly Ser Phe Phe Leu Tyr Ser Lys Leu Thr Val Asp Lys Ser
625                 630                 635                 640
Arg Trp Gln Gln Gly Asn Val Phe Ser Cys Ser Val Met His Glu Ala
                645                 650                 655
```

Leu His Asn His Tyr Thr Gln Lys Ser Leu Ser Leu Ser Pro Gly Lys
            660                 665                 670

Lys Asp Pro Lys Phe Trp Val Leu Val Val Val Gly Gly Val Leu Ala
        675                 680                 685

Cys Tyr Ser Leu Leu Val Thr Val Ala Phe Ile Ile Phe Trp Val Arg
    690                 695                 700

Ser Lys Arg Ser Arg Leu Leu His Ser Asp Tyr Met Asn Met Thr Pro
705                 710                 715                 720

Arg Arg Pro Gly Pro Thr Arg Lys His Tyr Gln Ala Tyr Ala Ala Ala
                725                 730                 735

Arg Asp Phe Ala Ala Tyr Arg Ser Leu Arg Val Lys Phe Ser Arg Ser
            740                 745                 750

Ala Asp Ala Pro Ala Tyr Gln Gln Gly Gln Asn Gln Leu Tyr Asn Glu
        755                 760                 765

Leu Asn Leu Gly Arg Arg Glu Glu Tyr Asp Val Leu Asp Lys Arg Arg
    770                 775                 780

Gly Arg Asp Pro Glu Met Gly Gly Lys Pro Arg Arg Lys Asn Pro Gln
785                 790                 795                 800

Glu Gly Leu Tyr Asn Glu Leu Gln Lys Asp Lys Met Ala Glu Ala Tyr
                805                 810                 815

Ser Glu Ile Gly Met Lys Gly Glu Arg Arg Arg Gly Lys Gly His Asp
            820                 825                 830

Gly Leu Tyr Gln Gly Leu Ser Thr Ala Thr Lys Asp Thr Tyr Asp Ala
        835                 840                 845

Leu His Met Gln Ala Leu Pro Pro Arg Glx
    850                 855

<210> SEQ ID NO 14
<211> LENGTH: 395
<212> TYPE: DNA
<213> ORGANISM: Artificial sequence
<220> FEATURE:
<223> OTHER INFORMATION: mIL7 (mouse IL7)

<400> SEQUENCE: 14
gagtgccaca ttaaagacaa agaaggtaaa gcatatgaga gtgtactgat gatcagcatc      60
gatgaattgg acaaaatgac aggaactgat agtaattgcc cgaataatga accaaacttt     120
tttagaaaac atgtatgtga tgatacaaag gaagctgctt ttctaaatcg tgctgctcgc     180
aagttgaagc aatttcttaa aatgaatatc agtgaagaat tcaatgtcca cttactaaca     240
gtatcacaag gcacacaaac actggtgaac tgcacgagta aggaagaaaa aaacgtaaag     300
gaacagaaaa agaatgatgc atgtttccta aagagactac tgagagaaat aaaaacttgt     360
tggaataaaa ttttgaaggg cagtatagcg gccgc                                395

<210> SEQ ID NO 15
<211> LENGTH: 121
<212> TYPE: DNA
<213> ORGANISM: Artificial sequence
<220> FEATURE:
<223> OTHER INFORMATION: linker

<400> SEQUENCE: 15

```
aggaggcggg ggttctggtg gaggcggaag cggtggcggg ggttcaggag gcggggttc      60 cggtggtggc ggcagtggtg gtggcggcag tggtggtggc ggcagtggtg gtggcggcag    120
t                                                                    121
```